(12) United States Patent
Wharton et al.

(10) Patent No.: US 7,677,244 B2
(45) Date of Patent: Mar. 16, 2010

(54) DRUG DELIVERY DEVICE AND METHOD

(75) Inventors: David Peter Wharton, Banksia Beach, Bribie Island (AU); Ben Huber, Clayfield (AU)

(73) Assignee: Medi-Stream Pty Ltd (AU)

( * ) Notice: Subject to any disclaimer, the term of this patent is extended or adjusted under 35 U.S.C. 154(b) by 1083 days.

(21) Appl. No.: 10/535,110

(22) PCT Filed: Nov. 14, 2003

(86) PCT No.: PCT/AU03/01526

§ 371 (c)(1),
(2), (4) Date: Dec. 27, 2005

(87) PCT Pub. No.: WO2004/045720

PCT Pub. Date: Jun. 3, 2004

(65) Prior Publication Data

US 2006/0124129 A1    Jun. 15, 2006

(30) Foreign Application Priority Data

Nov. 15, 2002 (AU) ............... 2002952707
Jul. 11, 2003 (AU) ............... 2003903586

(51) Int. Cl.
*A61M 11/00* (2006.01)
*A62D 9/00* (2006.01)
*B63C 11/00* (2006.01)
*B63C 11/22* (2006.01)

(52) U.S. Cl. ............... 128/201.27; 128/201.22; 128/200.14; 128/200.11; 128/207.14; 128/200.23

(58) Field of Classification Search ............ 128/200.22, 128/200.14, 200.21, 201.11, 201.22, 201.27, 128/201.28, 203.29, 204.11, 205.22, 206.28, 128/206.29, 207.14

See application file for complete search history.

(56) References Cited

U.S. PATENT DOCUMENTS

| 3,490,452 | A | * | 1/1970 | Greenfield | 128/200.23 |
| 4,031,887 | A | * | 6/1977 | Botos et al. | 128/205.12 |
| 4,304,229 | A | * | 12/1981 | Curtin | 128/201.11 |
| 4,433,684 | A | | 2/1984 | Sarnoff et al. | |
| 5,318,015 | A | * | 6/1994 | Mansson et al. | 128/200.22 |
| 5,996,579 | A | | 12/1999 | Coates et al. | |
| 6,014,972 | A | | 1/2000 | Sladek | |
| 6,116,238 | A | | 9/2000 | Jackson et al. | |
| 7,207,329 | B2 | * | 4/2007 | Bowden | 128/203.12 |
| 2003/0150450 | A1 | * | 8/2003 | Fitton | 128/200.24 |

FOREIGN PATENT DOCUMENTS

| JP | 2000-140114 A1 | 5/2000 |
| WO | WO 95/31240 A1 | 11/1995 |
| WO | WO 03/041774 A1 | 5/2003 |

* cited by examiner

*Primary Examiner*—Steven O Douglas
*Assistant Examiner*—Clinton Ostrup
(74) *Attorney, Agent, or Firm*—Tim Headley

(57) ABSTRACT

Breathing apparatus for medicating an airstream, compring a breathing apparatus (139), a medication chamber (138) adapted to store and discharge a therapeutic agent, a delivery pathway (141) between the chamber (138) and an intake air pathway and releasing means (145) for selectively discharging the therapeutic agent from the chamber (138) into the intake air pathway. The apparatus is particularly suited for scuba diving, snorkels, gas masks and filters. The invention is suitable for asthma sufferers but also extends to other respiratory diseases. Also claimed are a medication chamber for use in medicating an airstream and a method of medicating an airstream.

29 Claims, 27 Drawing Sheets

DRUG DELIVERY DEVICE AND METHOD

FIELD OF THE INVENTION

The present invention relates to a device and method for delivery of a drug or drugs to a target organ or subject via the respiratory or gastrointestinal system. Preferably, the invention relates to delivery of drugs to a target subject by entraining the drug in an air stream which may be either pressurised or at atmospheric pressure. More specifically, in one non-limiting aspect, the present invention relates to the delivery of a drug or drugs in a pressurised air stream when the recipient is in ambient conditions of increased or decreased atmospheric pressure and reliant on a pressurised respiratory gas supply such as when scuba diving under water. In a further aspect, the invention relates to a device and method for medicating an air supply at ambient air pressure such as, for example, but not restricted to, when a person is using a snorkel, a filter mask or similar. The device and method may have use in a wide range of applications where respiratory gases are directed to a person in a manner that channels the gases to either or both the mouth and nose.

BACKGROUND OF THE INVENTION

The development of self contained underwater breathing apparatus ("scuba") has revolutionised underwater diving for both recreational and professional divers. The simplicity and reliability of modern scuba gear has extended the range and scope of diving activities to a much broader spectrum of society than originally envisaged when the prototype was first successfully tested in 1943.

The range of available diving activities extends from simple recreational pursuits through to specialised activities such as cave, ice and wreck doing. In warmer waters and particularly in tropical and subtropical areas near coral reefs, there is a great demand for diving tuition and diving expeditions. Many people, including the inexperienced, seek the experience of general and introductory diving activities.

In order to be a suitable candidate for undertaking scuba diving, it is necessary to have at least reasonable health with no major relevant disease conditions. Perhaps the commonest obstacle to scuba diving is asthma, which is both a pervasive disease in society and an exclusionary condition when considering diving. The incidence of asthma has been estimated variously at 10% in Australia and New Zealand, 4-7% in the USA and 6-8% in the United Kingdom. Even mild signs of the disease may be sufficient to bar participation in scuba diving, as the obstructive effect of this condition can be very marked. It has been noted that asthma increases the risk of lung barotrauma and represents a contraindication to diving (Heritier and Russi, *Journal Suisse de Medicine* 123(5):161-165, 1993). This blanket exclusion has been questioned. A suggested approach of bronchodilator inhalation prior to diving has been given some consideration (Coetmeur et al., *Revue des Maladies Respiratoires* 18:381-386, 2001). But without any controlled studies, this approach runs the risk of inappropriate medication or, perhaps more significantly, medication at a time removed from the trigger event and onset of bronchoconstriction, thereby proving ineffectual.

Experienced diving instructors will relate many stories of otherwise seemingly perfectly healthy people being excluded from diving glasses and the rewards of a diving experience, even when those people are asymptomatic. One perceived risk for such a person participating in scuba diving is that a sudden onset of a severe attack at any depth, or even on the surface, could have catastrophic and even fatal consequences. As pressure increases by one atmosphere for every 10 meters of depth, even at a depth of 5 meters, a diver must accommodate a 50% increase in ambient pressure. Respiratory embarrassment, even at this relatively shallow depth, may have significant adverse consequences. One of the unpredictable aspects of asthma is that the severity of episodes of dyspnoea is highly variable and also unpredictable.

The problem is not confined to scuba diving and may also arise when a person is snorkelling. The onset of difficult breathing may arise on the surface or while diving below the water level. Similar problems may arise in people in other contexts when they are required to don respiratory apparatus. This situation may arise in occupations such as pilot or fire officer and in workers at risk of exposure to gas or hazardous chemicals.

Aerosol medications are extremely well known for effective therapeutic intervention in an asthma attack when a victim is in normal atmospheric conditions. However, to date, it has not been possible to provide access to such therapeutic agents under water in scuba diving or snorkelling or in gas masks used generally in industrial settings. Likewise, powder and liquid therapeutic agents may also be administered via the respiratory system.

It should be noted that while the following disclosure is directed primarily to scuba diving and snorkelling arrangements, it is possible to transfer the same device and method to a wider range of situations for use with pressurised or otherwise delivered or channelled respiratory air supplies. Also, the term drug is used in its widest sense to include agents that are both therapeutic and recreational and agents which may have a mechanical effect on the respiratory tract such as maintaining moisture content or providing a surfactant activity or similar. Further, reference to asthma is exemplary only and other respiratory diseases as well as other conditions treatable via the respiratory or gastrointestinal systems may also be suitable for application of the present invention. Indications for the invention may include diseases or physiological effects due to increases and decreases of ambient pressures such as nitrogen narcosis and C.N.S. effects due to increased partial pressure of compounds in inhaled gas where these conditions are treatable via the respiratory or gastrointestinal systems.

It would be advantageous to provide a means of delivering a drug to a patient in a pressurised or unpressurised air stream underwater or on or near the surface of a body of water or elsewhere.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers. Reference to "air" includes a reference to gas or gas combinations suitable for breathing. Relevant examples include Nitrox and Heliose products.

In one aspect, the invention resides in a modified breathing apparatus for medicating an airstream, said modified breathing apparatus comprising:

a breathing apparatus comprising one of a regulator suitable for delivering air from a source of compressed air, the regulator adapted for use in scuba gear, aircraft applications, gas masks, hazardous environments, mountaineering, power assisted respirators and other similar applications, a snorkel or part thereof, a rebreathing device or a self-contained breathing apparatus;

a medication chamber adapted to store and discharge a therapeutic agent;

a delivery pathway between the chamber and an intake air pathway of the breathing apparatus; and releasing means for selectively discharging the therapeutic agent from the chamber into the intake air pathway through the delivery pathway.

The breathing apparatus may comprise an arrangement, or part thereof, for underwater activity. The breathing apparatus may be a regulator suitable for delivery of air from a source of compressed air, either alone or in combination with another apparatus. The breathing apparatus may comprise a scuba arrangement or part thereof. The breathing apparatus may comprise a snorkel or part thereof. The breathing apparatus may comprise a gas mask, a filter mask, a respiratory mask or similar. The breathing apparatus may comprise a conduit for channelling inspiratory air. The breathing apparatus may comprise a rebreather which may be closed or semi-closed.

The therapeutic agent may be housed in a container, the container adapted to locate, at least partially, in the medication chamber.

The medication chamber may be formed integrally with the breathing apparatus. Preferably, the medication chamber is formed for releasable engagement with the breathing apparatus. The medication chamber is preferably sealed.

The modified breathing apparatus may further comprise balance means for substantially equalising pressure in the chamber with ambient pressure.

The medication chamber may form part of or be locatable in a regulator arrangement for a pressurised breathing apparatus. Alternatively, the chamber may be in operative proximity to a portion of a regulator arrangement for a pressurised breathing apparatus. The chamber may be arranged for cooperation with an airline of an under water breathing apparatus.

The container for housing the therapeutic agent may be a pressurised canister. The pressurised canister may have a release valve which is pressure activated to discharge the therapeutic agent. The container may deliver a preselected dosage of agent. The agent may be one or more of salbutamol (Ventolin®), albuterol, adrenaline, beconase (Becotide®), Seretide®, Flixomal®, glucose or any other suitable agent. The container may form part of or include a nebuliser arrangement, wherein intake of respiratory gases causes an aerosol to be produced and entrained in the intake air. The nebuliser arrangement may include a venturi assembly, Alternatively or additionally, the container may comprise a polymeric capsule, a gelatine capsule, a blister pack or other suitable arrangement adapted to house the therapeutic agent. The container is preferably sealed.

The therapeutic agent may be one or more of a solid, preferably a powder, a liquid or a gas. The therapeutic agent may be a volatile agent.

The delivery pathway between the chamber and an intake air pathway may arise simply from the chamber being disposed along the intake air pathway with discharge from the chamber directly into the intake air pathway. Alternatively, the chamber may communicate with the intake air pathway through at least one bore or channel. The pathway may be a detour air pathway adapted to direct some or all or the intake air through the chamber.

The bore or channel may include valve means operable to open and close the bore or channel. The valve means may be a slide lock. The slide lock may include locking means such as a locking nut to prevent unintentional activation. The slide lock may include a positioning device such as a pin for indicating when the slide lock is in suitable position to open the bore or channel. The valve means may comprise a rotatable flap. The valve means may comprise two or more apertures or channels movable between an out of alignment closed position and an aligned open position.

The device may include two or more delivery pathways between the chamber and an intake air pathway.

The breathing apparatus may comprise scuba gear or part thereof. The breathing apparatus may comprise a snorkel.

The balance means may comprise a compressed air supply source, an intake valve means, an outlet valve means and pressure deformable means for responding to variations between pressure inside the chamber and outside the chamber, such as water pressure, wherein the pressure deformable means will activate the inlet valve when outside pressure significantly exceeds chamber pressure and the outlet valve will release air when the chamber pressure significantly exceeds outside pressure.

Preferably, the compressed air source is an off-shoot of a primary air line of the breathing apparatus.

The releasing means may comprise a rotatable dial or control for activating a displacement mechanism to displace the pressurised canister and thereby activate the release valve of the pressurised canister. The displacement means may be a cam operated slide in the medication chamber.

Alternatively the rotatable dial or control may in operation displace a measured amount of therapeutic agent and position it in the delivery pathway or the intake air pathway. Further alternatively, the releasing means may comprise a pressure activated button for operating the release nozzle of the pressurised canister. The button may displace the canister or a seat co-operating with the canister to discharge the therapeutic agent. Displacement of the seat or canister may simultaneously clear one or more apertures to provide the delivery pathway. Alternatively or additionally, the button and/or rotatable dial or control may rotate a delivery chute into a discharge position from an inactive position. Rotation of the delivery chute may clear one or more apertures to provide the delivery pathway.

The modified breathing apparatus may further include counting means for indicating, at least approximately, the number of doses of therapeutic agent that have been discharged from a chamber or container. The counting means may be formed as one or more apertures in the chamber wall with movable indicia, such as numbers, visible therethrough. The counting means may indicate, at least approximately, the level of residual therapeutic agent. A second counter may track the number of canisters that have been placed in the device so as to indicate the unit's serviceable life span.

In a further aspect, the invention resides in a modified breathing apparatus for medicated respiration comprising:

an air supply line;

a second stage regulator chamber connected to the air supply line;

a medication chamber operatively connected to the second stage chamber by at least one air pathway;

a medication canister mounted in the medication chamber and arranged to discharge its contents into the air pathway;

a secondary air supply line originating from the air supply line and providing air to the medication chamber;

an intake valve for controlling air delivery to the medication chamber from the secondary air line;

an exhaust valve for discharging air form the medication chamber;

a deformable diaphragm located between ambient water and the medication chamber;

wherein;

the deformable diaphragm activates a release lever to provide air to the medication chamber when ambient water pressure exceeds the pressure of the medication chamber; and the exhaust valve releases air from the medication chamber when the air pressure of the chamber exceeds ambient water pressure.

The device may include a pathway control valve for opening and closing the at least one air pathway. The control valve may be a slide lock. The slide look may have an indicator seal for indicating when it has been used. The slide lock may be held in place by a lock nut. Alternatively or additionally, the device may have a trap door arrangement, a lever arm arrangement or a removable plug as the control valve.

Preferably, the device includes two communicating pathways from the medication chamber to the second stage chamber. The two pathways may be aligned with discharge apertures in the medication canister. The discharge apertures may be opened by pressure. Pressure may be applied by an operator through a deformable pad located in the medication chamber, preferably in a side thereof. The medication canister may discharge into the air flow pathway.

In a still further aspect, the invention resides in a pressurised canister for storing a therapeutic agent. The pressurised canister may be formed with a lower amount of agent and at higher pressure than known devices. Further, the canister may have at least two discharge apertures. The apertures may be adapted for simultaneous discharge or may include a mechanism for providing selected discharge through one of the apertures. The canister is preferably adapted for use in the modified breathing apparatus described above.

In another aspect, the invention resides in a snorkel with discharge means for discharging a therapeutic agent, the discharge means mounted to the snorkel for operation to medicate inhaled air; and control or releasing means for activating discharge of the therapeutic agent. The discharge means preferably discharges the therapeutic agent through a discharge pathway into an air inlet pathway. The discharge means may include a medication chamber adapted to store the therapeutic agent. The medication chamber may be formed integrally with the snorkel. The chamber may be fixed permanently to the snorkel. The chamber may be reversibly mounted to the snorkel. The discharge means may include a canister. The canister may be pressurised. The canister may have a therapeutic agent release mechanism activated by externally applied pressure. The chamber may house the canister. The medication chamber is preferably sealed.

The discharge means may comprise a nebulising arrangement. This discharge means may include a venturi airflow arrangement. The discharge means may comprise an arrangement for dispersing a powder into the air inlet pathway.

The discharge means may be located eternally of the air pathway in the snorkel. Alternatively, the discharge means may be positioned within the air pathway.

The therapeutic agent may be one or more of albuterol, salbutamol, beconase, adrenaline aminophyline, glucose or other suitable compound or mixture.

The control or releasing means may include a rotatable control barrel. The barrel may be formed as a semi-cylindrical or longitudinally sectioned cylindrical device. The barrel may be movable form a first position to occlude an air pathway between a nozzle of the canister and a mouthpiece of the snorkel to a second position to open the air pathway. The barrel may be rotated by a finger operated lever or twist grip. The barrel may be rotatably mounted at each end. When rotated, the barrel may also turn the medication chamber.

The canister may be mounted in a medication chamber connected to the main snorkel. The medication chamber may be sealed to prevent or resist the ingress of water. The canister is preferably operated by application of externally applied pressure resulting in opening of an outlet valve in the canister. The canister may contain albuterol, salbutamol, beconase, adrenaline aminophyline, glucose or other suitable compound or mixture.

The discharge pathway may be opened by an alignment of a void in the control barrel and a vent in a wall of the main snorkel. The discharge pathway may be opened by alignment of an aperture in a slideable piston and a vent or aperture leading into the air pathway.

In an alternative embodiment, the control barrel may be mounted in the medication chamber. The medication chamber may be closed by a screw threaded end cap. The end cap is preferably sealed. The screw threaded end cap may include a deformable membrane for applying pressure to an end of the medical canister to thereby discharge a dose or therapeutic agent. The medication chamber may include a water trap.

The discharge means may comprise a nebuliser arrangement. The nebuliser arrangement may include a venturi assembly for dispersing the therapeutic agent.

Alternatively, the discharge means may comprise an arrangement for dispersing a powder or liquid. The arrangement may include a rotatable blade or blades for dispensing a powder or liquid into an intake air stream.

The control means may include a flow control valve for directing air through a detour air pathway additional to the main air pathway of the snorkel.

In still a further aspect, the invention resides in a medication chamber for use in medicating an air stream in an air channelling device which may comprise one of a regulator suitable for delivering air from a source of compressed air, the regulator adapted for use in scuba gear, aircraft applications, gas masks, hazardous environments, mountaineering, power assisted respirators and other similar applications, a snorkel or part thereof, a rebreathing device or a self-contained breathing apparatus, the medication chamber comprising:

an outer housing defining an internal chamber containing a therapeutic agent;

mounting means for fixing the medication chamber to the air channelling device;

at least one delivery path from the internal chamber externally and adapted to deliver the therapeutic agent to an air pathway in the air channelling device; and releasing means for releasing the therapeutic agent from the internal chamber.

The outer housing may be formed of one or more of plastic, polyvinyl chloride, PEEK, alloy, titanium or other suitable material. It may be formed in two interengageable sections. The two sections may be screwed threadably engaged.

The therapeutic agent may be any suitable agent including albuterol, salbutamol (Ventolin®); Beconase (Becotide®), adrenaline, aminophylline, or glucose.

The therapeutic agent may be held in a pressurised container with the release valve. The therapeutic agent may be a solid, liquid or gas.

The mounting means may comprise one or more recesses or slots for receiving a fixing device such as a screw and/or guide tab. The medication chamber may be dimensioned to locate in a recess, sleeve or bore in the air channelling device.

The at least one delivery path may be an outlet channel. The outlet channel may communicate with the release valve of the pressurised container. The releasing means may be a rotatable dial for activating a cammed mechanism to displace the canister and operate the release valve. Alternatively, the cammed mechanism may operate a slideable seat to activate the release valve of the canister. The releasing means may be a pressure activated button for displacing the canister or the seat and activating the release valve.

The releasing means may comprise a mechanism for providing a solid, particularly a powder, to the air pathway. The mechanism may comprise a geared arrangement for advancing a blister pack and presenting a powered agent container therein to the air pathway. Alternatively, the mechanism may comprise a rotatable dispenser for dispersing or dispensing a powdered agent to the air pathway. The mechanism may further comprise a valve operable to open or close the delivery pathway.

The air channelling device may be a scuba regulator, a snorkel, a breathing apparatus such as a respirator, a mask, a filter or similar. The channelling device 2 may also comprise a conduit positionable in engagement with the medication chamber and adapted to discharge directly into a user's mouth or nose. The conduit may have an angular deviation in its lumen. The conduit may further comprise a cap mounted to its external outlet and adapted for removal for use. The cap may occlude an accessory air inlet aperture adapted to provide a flow pathway to entrain the therapeutic agent.

The outer housing may include indication means for indicating, at least approximately, the content status of the internal chamber. The indicator means may comprise a counting arrangement which is advanced by every discharge of therapeutic agent. The counting arrangement may be returned to zero by disassembly of the outer housing.

The outer housing may further comprise an inlet pathway for receiving a pressurised air supply. The outer housing may also comprise an outlet valve for discharging air from the internal chamber when air pressure inside the chamber exceeds pressure outside the chamber.

In yet another aspect, the invention may reside in a method of medicating an air stream in a breathing apparatus which may comprise one of a regulator suitable for delivering air from a source of compressed air, the regulator adapted for use in scuba gear, aircraft applications, gas masks, hazardous environments, mountaineering, power assisted respirators and other similar applications, a snorkel or part thereof, a rebreathing device or a self-contained breathing apparatus, the method comprising the steps of:

- mounting a chamber containing a therapeutic agent to a breathing apparatus; and
- introducing one or more doses of the therapeutic agent into an inlet pathway for inspiratory air.

Mounting the chamber may comprise forming the chamber integrally with the breathing apparatus or forming a separate chamber and reversibly or permanently mounting it to the breathing apparatus.

The method may include the step of positioning a container holding the therapeutic agent in the chamber. The container may be a pressurised container.

Introducing one or more doses of the therapeutic agent may include the step of activating an agent releasing mechanism such as depressing a button, rotating a control dial, knob or lever, or other voluntary action to release a dose of therapeutic agent. Introducing the therapeutic agent into an inlet pathway may comprise the step of introducing the agent directly into the inlet pathway from the chamber or, alternatively, through a delivery air pathway from the chamber to the inlet pathway.

BRIEF DESCRIPTION OF THE DRAWINGS

FIG. 1 is a perspective view of a modified second stage regulator of the present invention.

FIG. 2 is a perspective view of the device of FIG. 1 with medication chamber removed.

FIG. 3 is a rear view of the arrangement of FIG. 1.

FIG. 4 is a sectional view of the arrangement of FIG. 3 taken along line AA.

FIG. 5 is a side view of a removable chamber for use with a breathing apparatus.

FIG. 6 is a perspective view of the medication chamber of FIG. 5.

FIG. 7 is a sectional view taken along the line BB of FIG. 5 when the medication chamber is at rest.

FIG. 8 is a similar view to FIG. 7 but when the medication chamber is activated.

FIG. 9 is a perspective view of an alternative embodiment of a medication chamber.

FIG. 10 is a side view of the medication chamber of FIG. 9.

FIG. 11 is a sectional view of the medication chamber of FIG. 10 taken along the line CC.

FIG. 12 is a rear view of a regulator and medication chamber with diaphragm removed.

FIG. 13 is a perspective view of an inlet assembly of a regulator and medication chamber.

FIG. 14 is a side view of a modified inlet assembly.

FIG. 15 is a sectional view of the arrangement of FIG. 14.

FIG. 16 is a front perspective view of a modified snorkel base.

FIG. 17 is a top view of the arrangement of FIG. 16.

FIG. 18 is a side view of the snorkel base of FIG. 16.

FIG. 19 is a rear view of the modified snorkel base of FIG. 16.

FIG. 20 is a sectional top view of the arrangement of FIG. 19 taken along the line DD.

FIG. 21 is a top view of an alternative arrangement of a modified snorkel base.

FIG. 22 is a rear view of the arrangement of FIG. 21.

FIG. 23 is a sectional side view of the arrangement of FIG. 22 taken along the line EE.

FIG. 24 is a sectional top view of the arrangement of FIG. 22 taken along the line FF.

FIG. 25 is a perspective view of a modified snorkel.

FIG. 26 is a top view of a further alternative snorkel base arrangement.

FIG. 27 is a rear view of the arrangement of FIG. 26.

FIG. 28 is a sectional top view of the arrangement of FIG. 27 taken along the line GG.

FIG. 29 is a perspective view of a modified snorkel with medication chamber attached.

FIG. 30 is a perspective view of the arrangement of FIG. 29 with medication chamber removed.

FIG. 31 is a perspective view of a further alternative embodiment of a modified snorkel.

FIG. 32 is a sectional side view of the arrangement of FIG. 31.

FIG. 33 is a sectional side view of the base arrangement of FIG. 32 with the canister activated.

FIG. 34 is a perspective view of further embodiment of a modified snorkel.

FIG. 35 shows a sectional side view of the arrangement of FIG. 34 when inactive.

FIG. 36 shows the arrangement of FIG. 35 when activated.

FIG. 37 shows a sectional top view further of an embodiment of a modified regulator adapted for use with a powder.

FIG. 38 shows a side view of the arrangement of FIG. 37.

FIG. 39 shows the modified regulator of FIG. 37 when in use.

FIG. 40 shows a sectional view of a further embodiment of a modified regulator for use with a powder medication.

FIG. 41 shows the arrangement of FIG. 40 when in use.

FIG. 42 is a sectional top view of a dry powder medication arrangement for a snorkel.

DETAILED DESCRIPTION OF THE DRAWINGS

Figure 1:
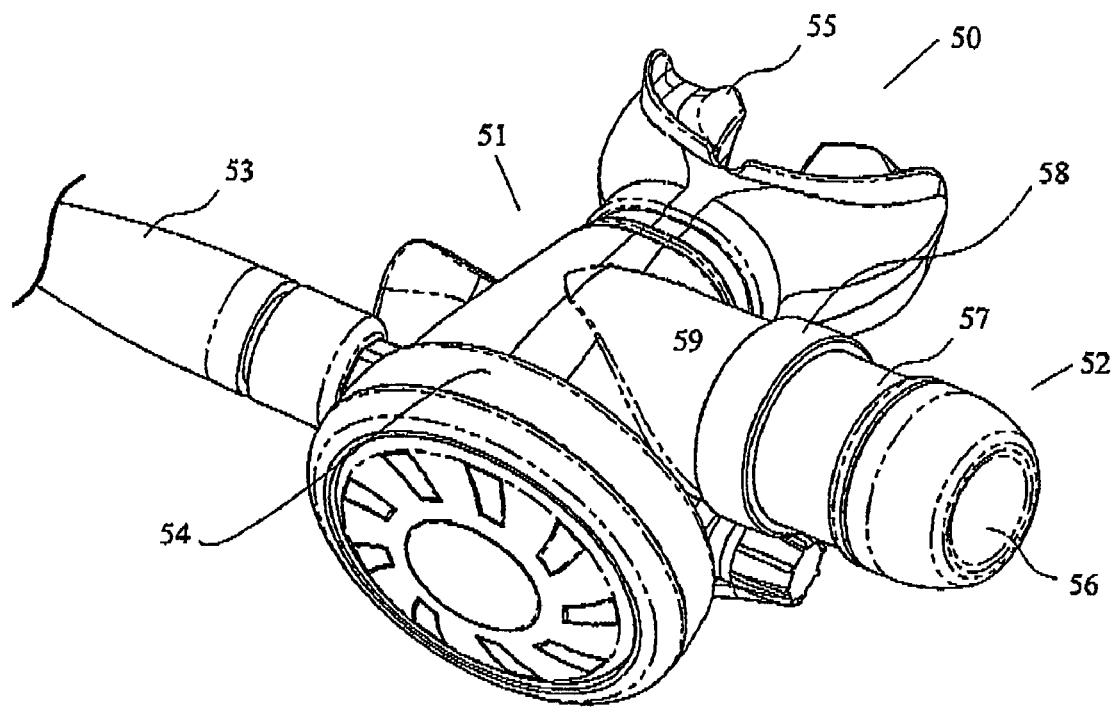

Scuba diving developed from the technological advance of providing an oxygen mixture under high pressure in a tank coupled with a pressure reducing mechanism for presenting the mixture to a person's lungs sufficiently decreased in pressure to avoid injury. The principle development related to the production of a regulator for use with either compressed air (78% nitrogen, 21% oxygen) or an oxygen enriched nitrogen oxygen combination such as NITROX, which is a name applied to a range of suitable mixtures. However, the most common range is 64-68% nitrogen and 32-36% oxygen. This gas mixture will be typically held in a metal cylinder which holds approximately 2,200 liters of mixture at around 180-230 atmospheres of pressure (ATM).

A regulator is usually provided having a first stage and second stage function. The regulator is adapted to provide air on demand by a user and also reduce the pressure as required.

The first stage of a regulator may attach to the cylinder of air and is designed to reduce pressure from the tank, usually on average at around 204 ATM, to an intermediate pressure of around 9.5 ATM.

A length of flexible extendible hose is usually then provided to connect the first stage to the second stage of the regulator. The second stage is adapted to reduce the mixture from 9.5 ATM to ambient water pressure which is typically in the range of 1-5 ATM depending on depth. The second stage also includes a mechanism for providing air which is activated by inhalation by the diver or, in some circumstances, has an override for providing air continuously. Such a need may arise in an emergency situation.

The structure of the first stage includes high pressure and intermediate pressure chambers which have either a valve/diaphragm combination or a piston both of which are affected by water pressure.

High pressure air is delivered to the first chamber but is subject to controlled release into the second chamber from the action of the diaphragm or piston.

The act of breathing will decrease pressure in the secondary chamber leading to an imbalance between the pressure of the air in the chamber and the pressure of surrounding water. A resilient diaphragm may be deformed to activate a push valve, thereby clearing a seat and allowing high pressure air from the first chamber into the second chamber. An alternative arrangement uses a somewhat similar function but is based on a hollow piston which moves into and out of register with a cooperating seat with an alternatively closed and clear connecting passageway.

The second stage of the regulator is located adjacent and includes the mouth piece. The second stage has a chamber with a rubber diaphragm exposed to ambient water pressure and an inner valve that is connected to a moveable lever. The second stage also includes an exhaust valve and often has a purge button.

On inhalation, the pressure within the second stage drops below the ambient water pressure. As a result, the diaphragm is distorted and comes into contact with the lever which is pivotally mounted and is consequently rotated, thereby clearing an inlet line from the first stage of the regulator. This air is inhaled.

On expiration, the pressure in the second stage of the regulator is increased leading to closure of the air inlet, pressurisation of the diaphragm away from the lever and opening of the exhaust valve.

The above cyclical process is performed continuously during use of the breathing apparatus. The purge button may be used to clear water from the mouth piece and the second stage chamber by introduction of a large quantity of pressured air or gas mix.

The following description is given by way of example of the preferred embodiments only and should not be viewed as restricting the scope of the invention. A skilled person will understand the theory and principle of the invention can be modified and varied in use and practical application.

Referring to FIG. 1 there is seen an example of a modified breathing apparatus in the form of modified regulator 50 comprising a regulator 51 and medication chamber 52. The regulator comprises an inlet airline 53 or primary airline feeding into the regulator proper 54 which discharges through mouthpiece 55. The medication chamber 52 has an end cap 56, side wall 57 and mounting collar 58. The end cap 56 in this embodiment is a push button for activating release of the therapeutic agent.

It is preferred if the chamber 52 is demountable and it may be supported in place by the mounting collar 58 which may engage a threaded section of branch 59. Alternatively the collar may allow the chamber to be opened and may simply act as a stop against branch 59. The chamber may be fixed in position by a positive fixing means such as a grub screw, a bayonet fitting or similar. The relationship between the chamber and branch should preferably provide a water tight seal. In one embodiment, the chamber may be fixed permanently to the regulator and may be formed integrally with it.

Figure 2:
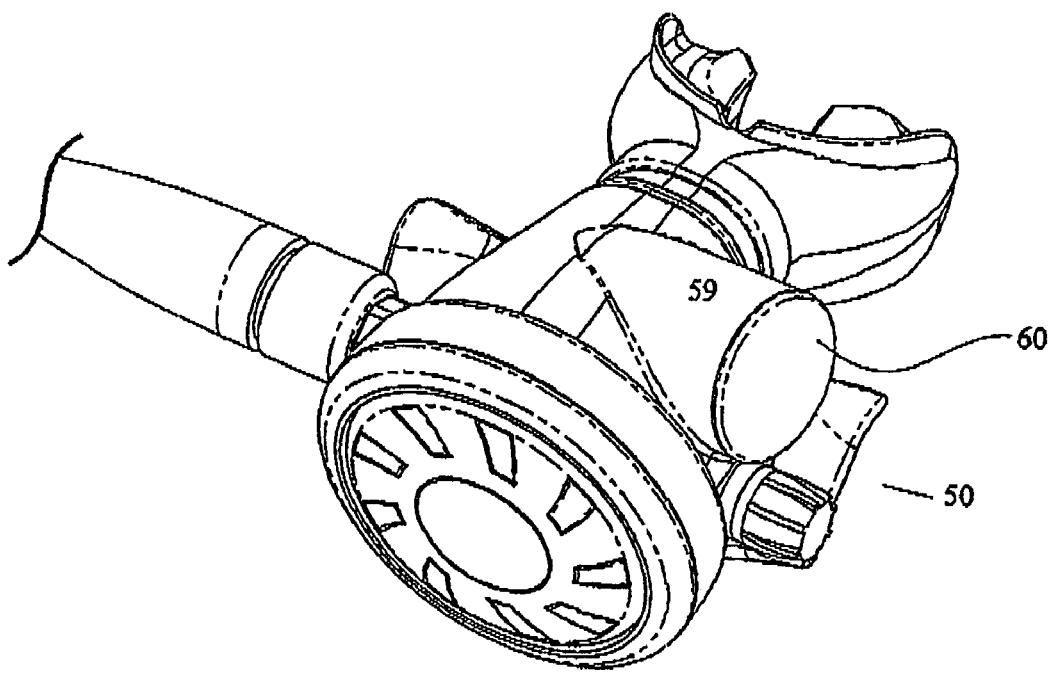

In FIG. 2 the chamber 52 has been removed and branch 59 has been closed with sealing cap 60. The demountability of the chamber 52 allows versatility in the modified breathing apparatus and it may be used for standard operation for people who are unaffected by asthma or similar diseases or who do not require any medication, Additionally, demountability of the chamber 52 allows easy replacement of the medication container which will be described more fully below.

Figure 3:
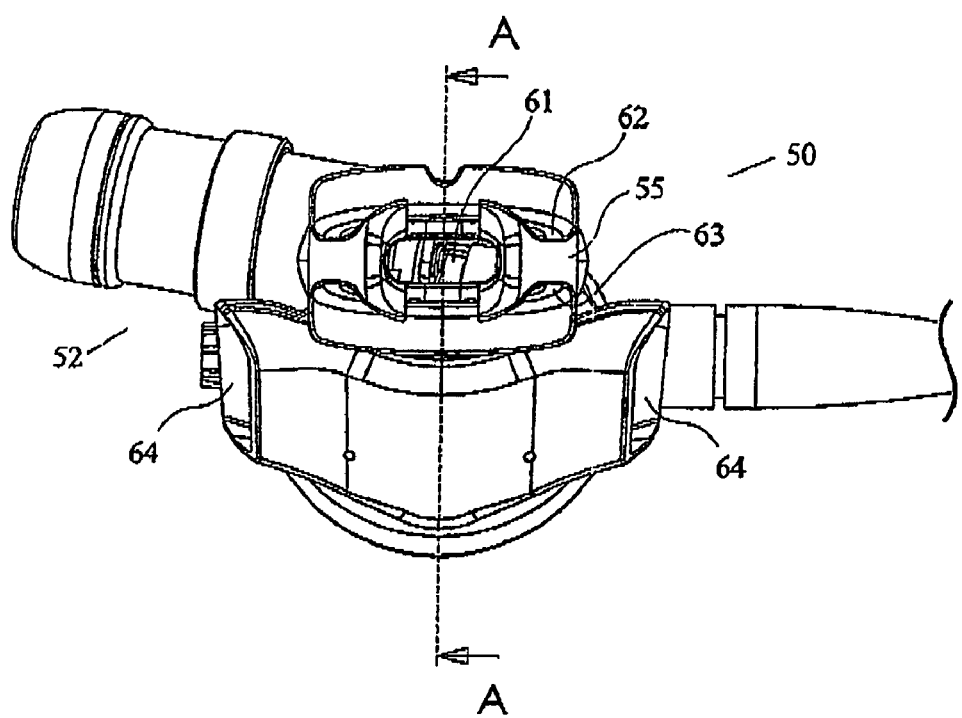

In FIG. 3 the mouth piece 55 is seen. It is preferred if the mouthpiece is adapted to maintain separation between a user's teeth. In this regard, it may be formed with an inlet aperture 61 provided by a users teeth locating on upper shield 62 and lower shield 63 thereby providing separation of the user's teeth and allowing any medication full access to a user's mouth rather than being coated on their incisors. Discharge apertures 64 are seen for exhaust gases from the modified regulator 50.

Figure 4:
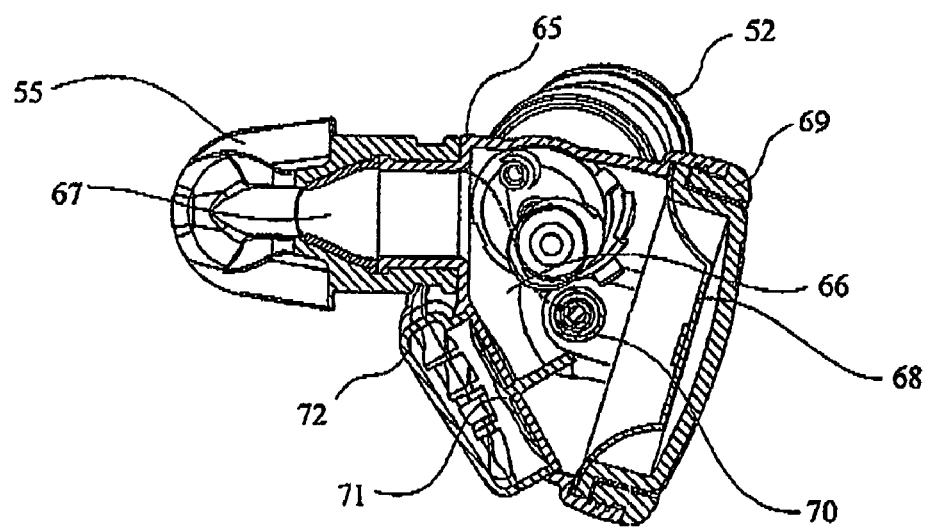

A sectional view is seen in FIG. 4 which shows the chamber 52 mounted to a main body 65 which defines internal chamber 66. The internal chamber communicates through a mouthpiece spacer 67 to the mouth piece 55. A diaphragm 68 is locked in place by a diaphragm lock ring 69. The diaphragm cooperates with the inlet assembly 70 to control gas inlet into the internal chamber 66. A main purge valve 71 is provided for purging any water from the internal chamber 66 through the exhaust apertures 72 and subsequently through the discharge apertures 64 of FIG. 3.

Figure 5:
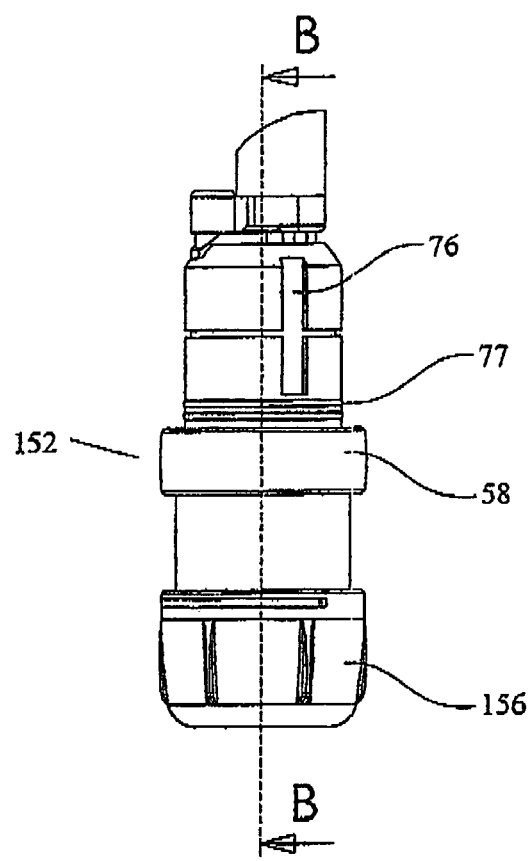
Figure 6:
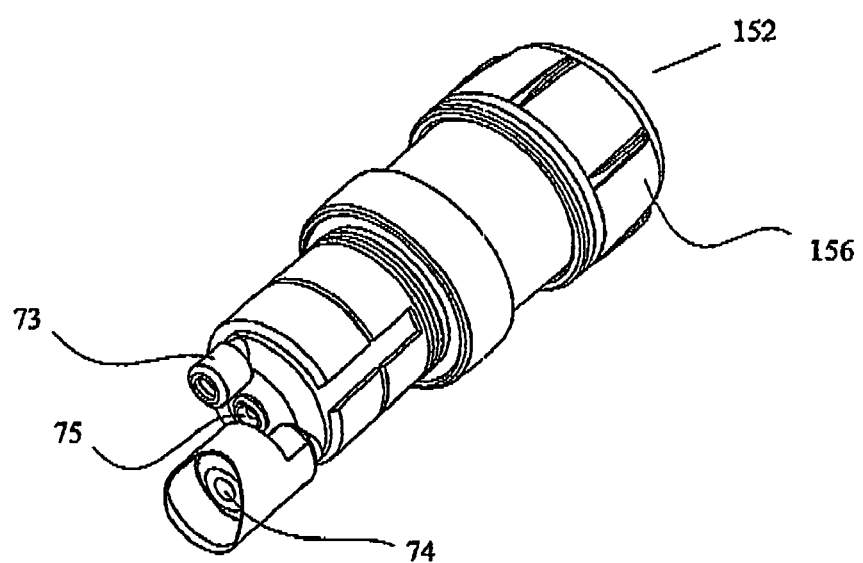

A second medication chamber 152 is seen in FIGS. 5 and 6 and comprises a twist cap end 156 an air inlet 73, a purge valve 74 and a nozzle outlet 75. The chamber also has a mounting recess 76 configured to locate the chamber in appropriate orientation in the breathing apparatus. The chamber may be positioned with the recess 76 aligned with a co-operating tab (not shown) in the breathing apparatus. The chamber may then be slid into position in the branch or any other formation adapted to locate it in the breathing apparatus. The chamber may be locked in position by a grub screw or similar. The mounting collar 58 is seen. Two O-rings 77 may be located distally to the mounting collar and provide sealed engagement in to the branch 59 previously described. The medication chamber is sealed to prevent or resist penetration by water, dust, fine particulate matter, mud or similar. The chamber may also be insulated to resist temperature fluctuations. Insulation may arise from an external coating or from the nature of the material used to form the housing. Formed polymers may be used or any other suitable material.

Figure 7:
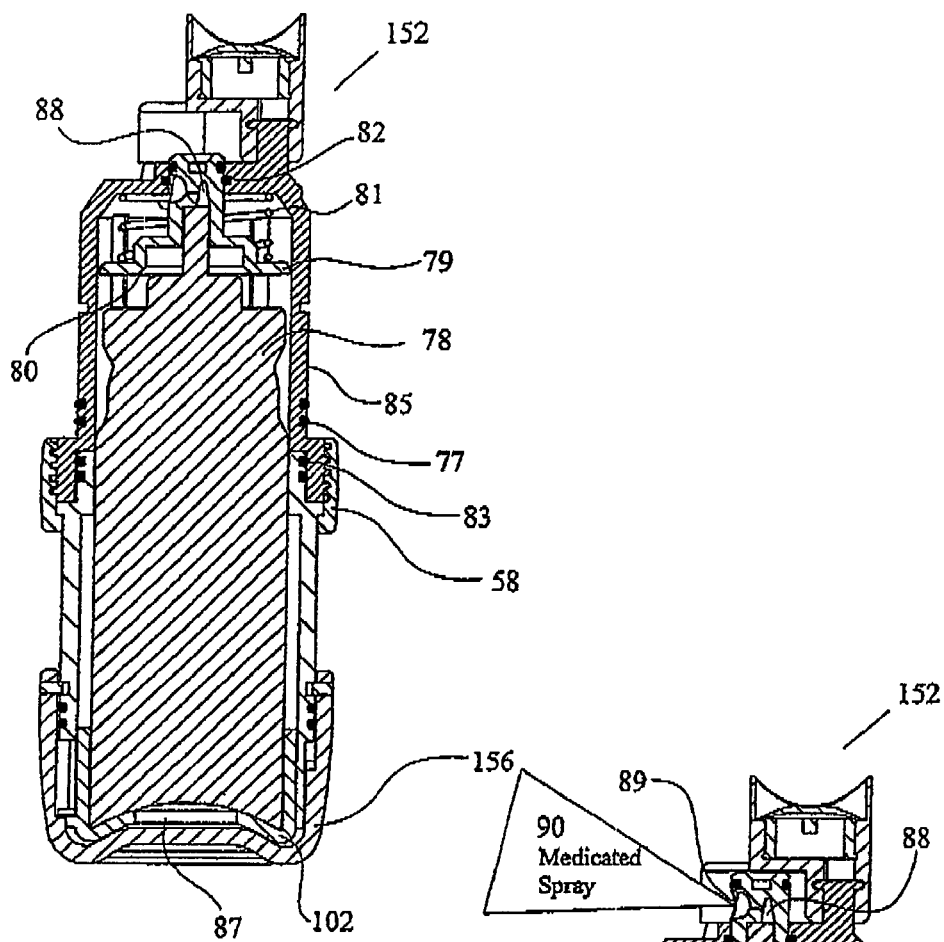

The sectional view in FIG. 7 shows the chamber 152 at rest. A pressurised canister 78 contains a suitable medication which may be salbutamol, beconase, adrenaline or any other therapeutic agent suitable for ingestion through the oral mucosa, the tongue, the gastrointestinal tract or the respiratory tract. As can be seen in this view, the collar 58 engages a thread in the wall of the chamber to provide a means of breaking the chamber into two components and removing the canister 78 for replacement. The twist end cap 156 is operable to provide an upwardly displacing action on the canister 78. In a preferred embodiment, a 90° C. turn translates to approximately 8 millimeters displacement of the canister. The canister sits against a seat 79 at its uppermost shoulder 80. The seat 79 is resiliently biased by a spring 81 to an inactive position. O-ring seals 82 resist ingress of water or other material into the chamber 152.

However in the event that this occurs, the chamber may be purged of excess fluid through the air inlet 73 and purge valve 74 (in FIGS. 5 and 6).

Further O-rings 77 are provided to seal the section of the body of the chamber that inserts into the breathing apparatus. This section is the internal body section 85. The break in the chamber at the collar 58 provides a potential inlet for moisture and may be addressed by additional O-rings 83 which provide a seal when the two halves are engaged.

Figure 8:
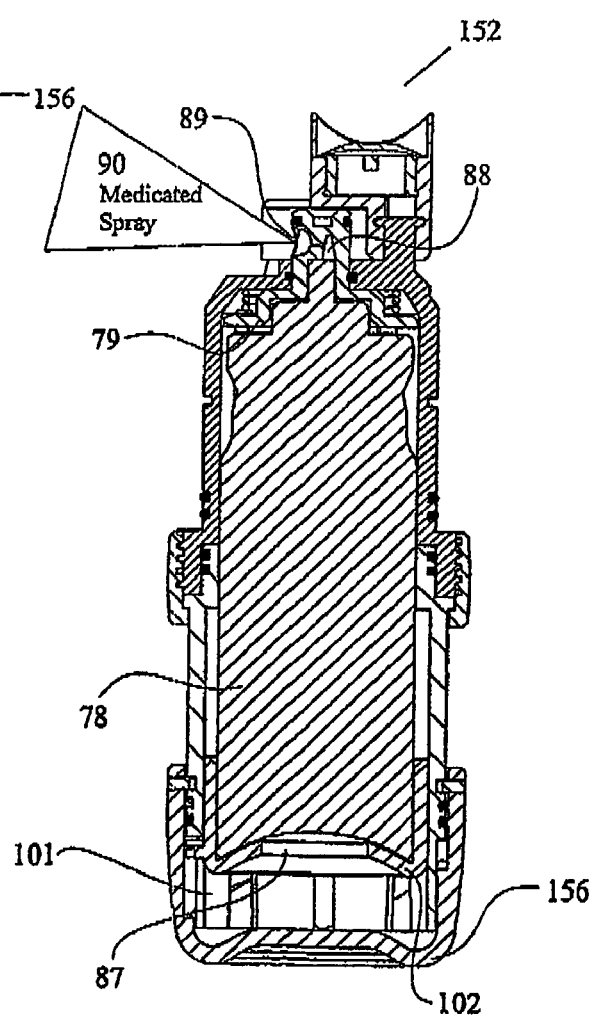

In FIG. 8, the twist action end 156 has been rotated to provide displacement of the end button 87 thereby leading to displacement of the canister 78 and the seat 79 which operates somewhat like a piston. Displacement of the seat and canister leads to alignment of a spray nozzle 88 with an outlet aperture 89 to provide a medicated spray 90. The twist action end 156 operates a cammed arrangement to displace the end button 87 to a maximal position before the cammed arrangement resets itself. Rotation of the twist cap 156 leads to movement in a cammed or saw toothed sleeve 101. As the sleeve, rotates, the toothed sleeve 101 slides the piston 102 and button 87 away from the base as a sloped leading surface of the saw toothed arrangement slides past an edge of the button 87 or piston 102. Maximal displacement is obtained at the point of the tooth before further advance leads to a drop over the steeper side of the tooth to re-set at the starting position.

In one aspect, the invention may reside in the medication chamber as described above, and extends to an embodiment provided with a fitting that allows easy dismounting and relocation of the chamber. The chamber may be moved from regulator to regulator or onto an alternative breathing apparatus such as a gas mask or indeed to a snorkel. The latter application may require some minor modification as described subsequently.

In use, an operator simply twists the end cap 156 to provide discharge of a single medicated dose. Additional twisting will result in further single dose applications. In a preferred embodiment, the chamber will feature a counter or indicator of remaining dosage. Each time the twist cap is operated, an indicator device may be advanced to provide an indication of changes from a high level of remaining doses towards a low level of remaining doses. Colouring may be used to indicate the difference. For example, green colouring may be used for high levels of medication in the canister and hence low usage. Orange may indicate ongoing and medium level usage. Red may indicate the need for replacement or caution in use. Other indicators such as a broad to narrow pattern may also be used for a similar purpose. Individual numbers may be used as indicators.

Figure 9:
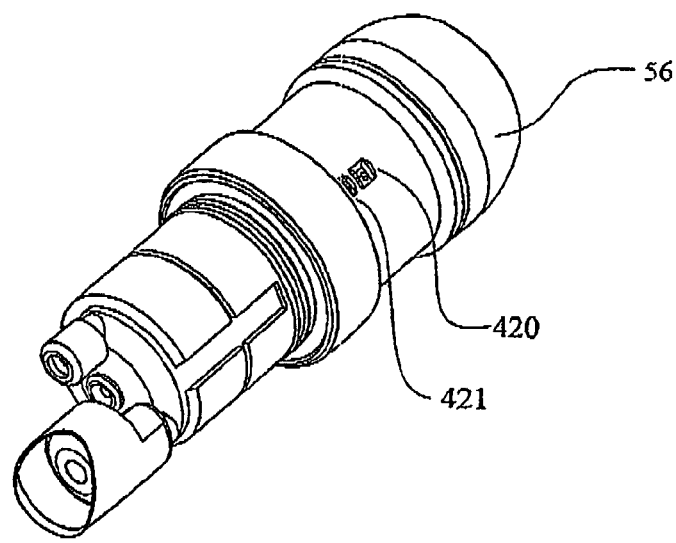
Figures 10, 11:
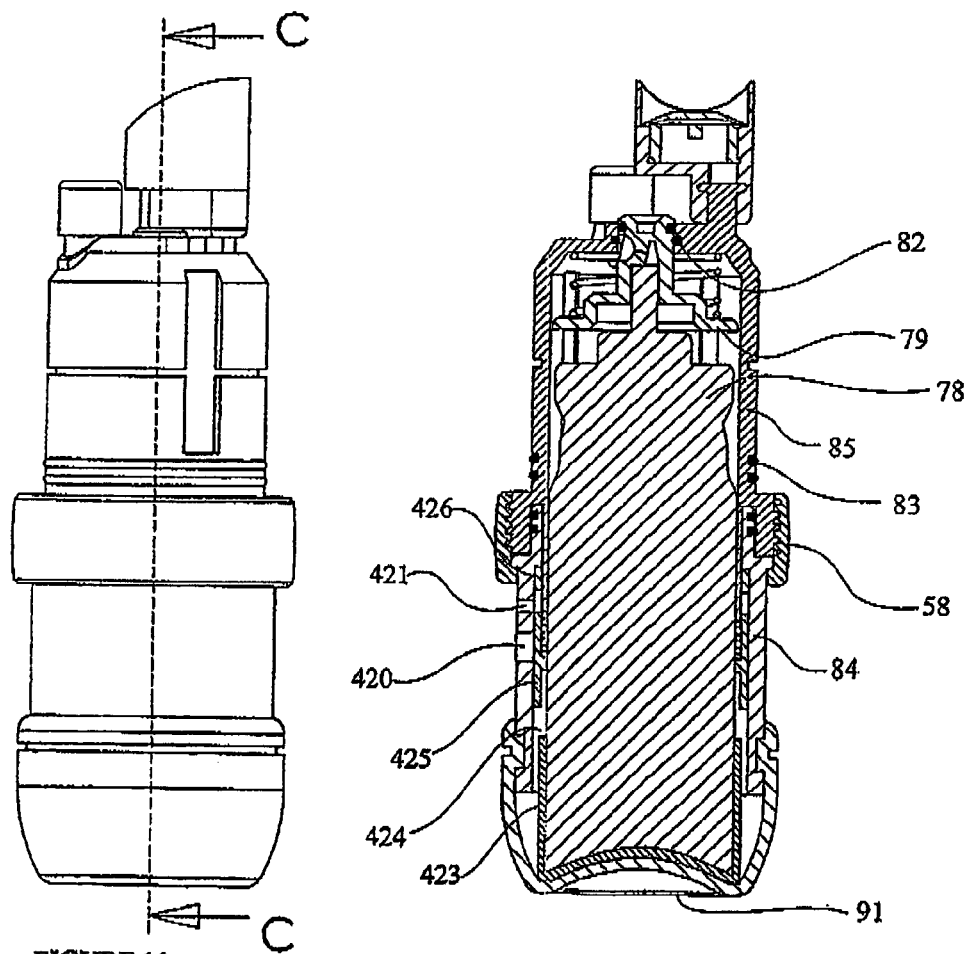

FIGS. 9 and 10 show a chamber similar in many respects to that of FIG. 1. In this instance, the end cap 56 is a push activated end cap. The components of the canister are otherwise very similar to that described in relation to FIGS. 5 and 6. However, in this case, a user simply depresses a push action end 91 which may be a deformable cover such as a rubber cap. An indictor or counter is shown with a number window 420 and range window 421. The number window 420 is arranged to record the number of depressions of the push action end 91. Any simple mechanical arrangement may be used to provide for the device to advance or otherwise for its activation. The range counter 421 provides an indication as to whether the canister is towards the high or low range of reserve. Alternatively the range counter may be advanced on separation of the chamber into two components. For example, the indicator may have four quadrants of different colour. Separating the interengageable halves of the chamber may advance the indicator to the next colour by a single mechanical trip. At the end of the fourth period of use, the chamber may be discarded. Alternatively, four periods of use may indicate the internal canister should be discarded irrespective of the number of doses dispersed.

Figure 12:
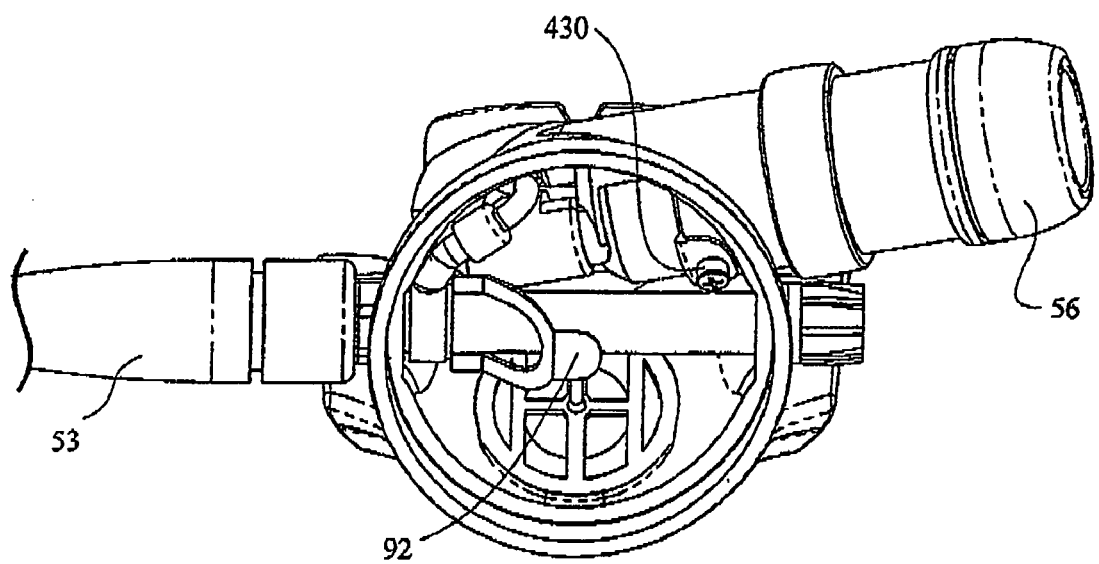
Figure 13:
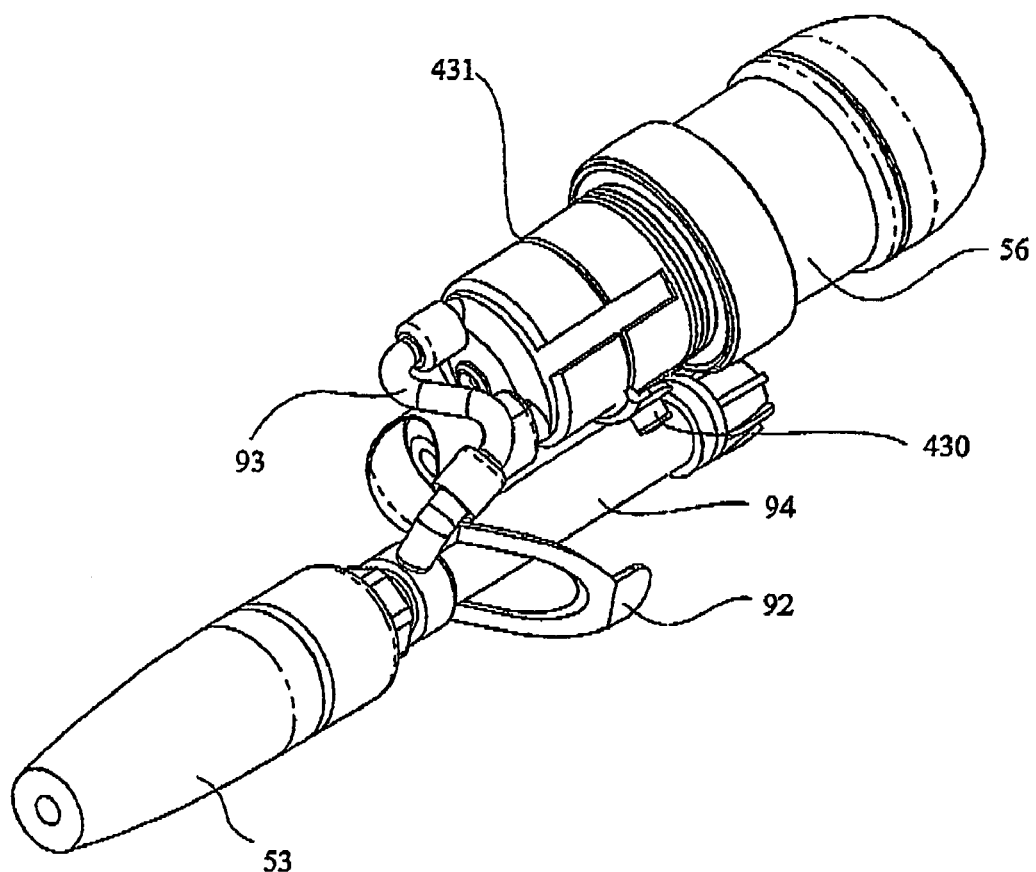

The sectional view of FIG. 11 also shows one arrangement of the counter with aperture 421 for the range counter and aperture 420 for the number window. Depression of the end 91 causes the sleeve 423 to cover gap 424 and engage sleeve 425 which is configured to rotate on contact and advance the number window counter 426 to show a new number. At the same time the range counter may be advanced. Alternatively, the range counter may be advanced by disassembly of the chamber to provide an indication of the episodes of use. In FIG. 12 the diaphragm has been removed and a valve opening arm 92 in an inlet assembly can be seen located inwardly of the airline 53. The arrangement is also seen in FIG. 13 wherein the valve opening arm 92 is operable by deformation of a diaphragm to allow inlet gases from the line 53 to be fed into a chamber (not shown) of a breathing apparatus.

Figure 14:
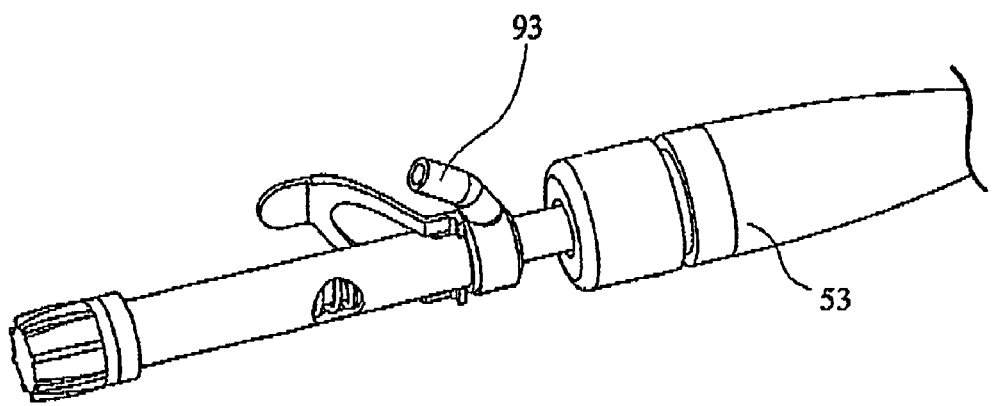
Figure 15:
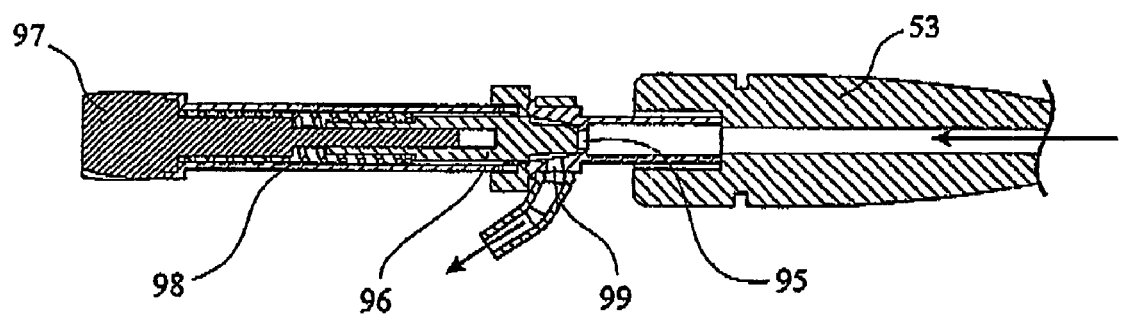

An offshoot airline 93 arises from the main airline 53 and connects the inlet assembly 94 with the medication chamber 66. Activation of the valve opening arm 92 will lead to air being delivered into the chamber of the regulator as well as into the medication chamber 56. The modified arrangement of the inlet assembly is also seen in FIGS. 14 and 15. The offshoot airline 93 arises down stream from the valve seat 95. Air is received through the airline 53 from a first stage regulator (not seen). The pressure for activation of the sliding valve 96 may be adjusted by adjustment control knob 97 which tensions or releases spring 98. A bleed off point 99 redirects some airflow to equalise the medication chamber to the pressure of the internal chamber.

Also visible in FIG. 12 is a retention screw and clamp 430 which may be advanced in to slot 431 to lock the chamber into position. The clamp is preferably formed with a tongue for location in the slot. Tightening of the retention screw will then tension the chamber into position. Other methods of fixing the chamber in position may also be applied.

Figure 16:
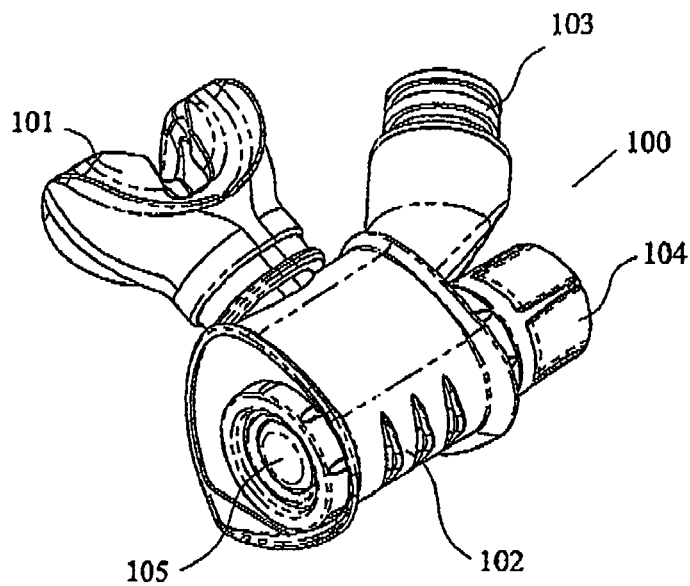
Figure 17:
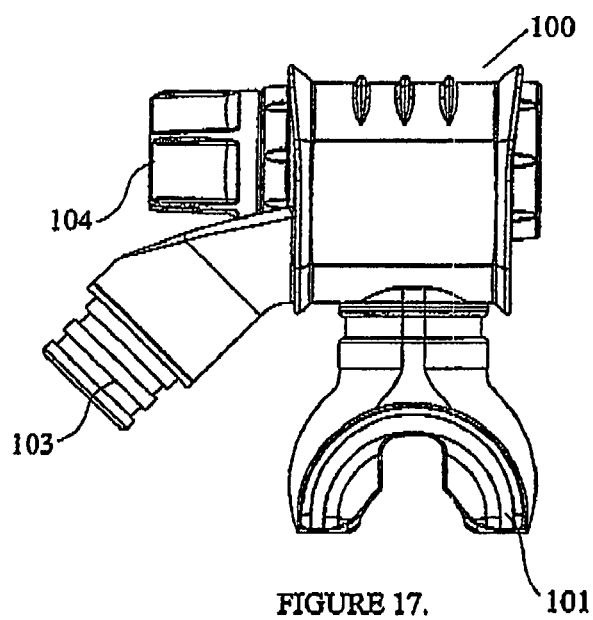
Figure 18:
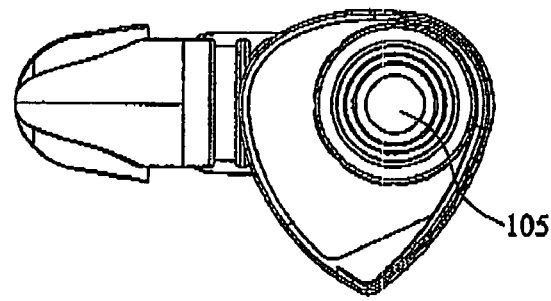
Figure 19:
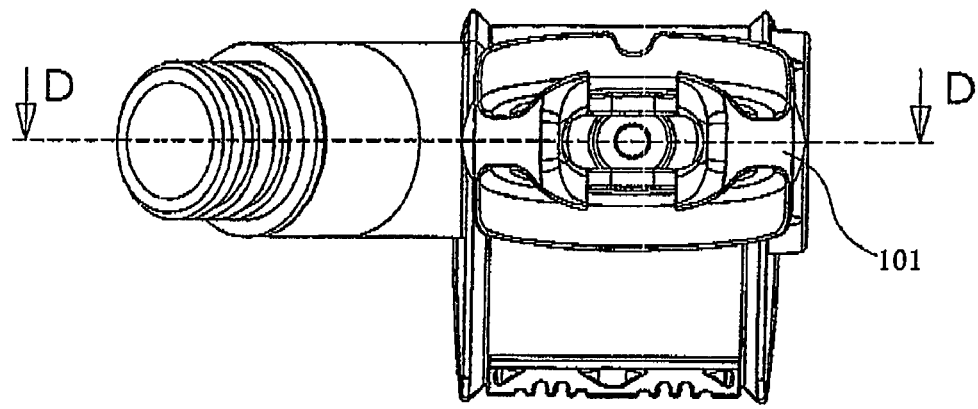

The present invention is also very well suited for use with a snorkel as is shown in FIG. 16 and subsequently. A modified snorkel or snorkel base 100 is seen in FIG. 16 comprising a mouth piece 101, a body 102, a pipe mounting 103 and medication chamber 104. FIG. 17 is a top view of the same arrangement. FIG. 18 is a side view and FIG. 19 is a rear view in which the structure of the mouth piece 101 is again highlighted for providing an effective space between the user's teeth. It is clear of course that a standard mouth piece may also be used. However, the anatomical placement of the user's teeth in a standard mouth piece may provide some impediment to effective or maximal ingestion of the medication. An activation button 105 is also apparent in these views.

Figure 20:
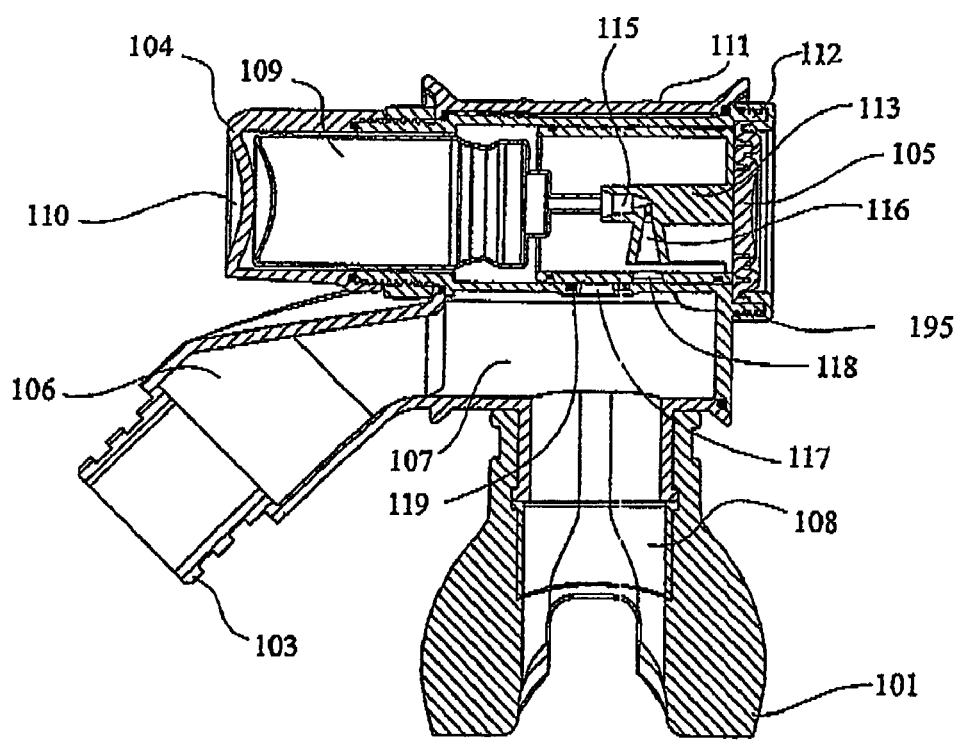
Figure 21:
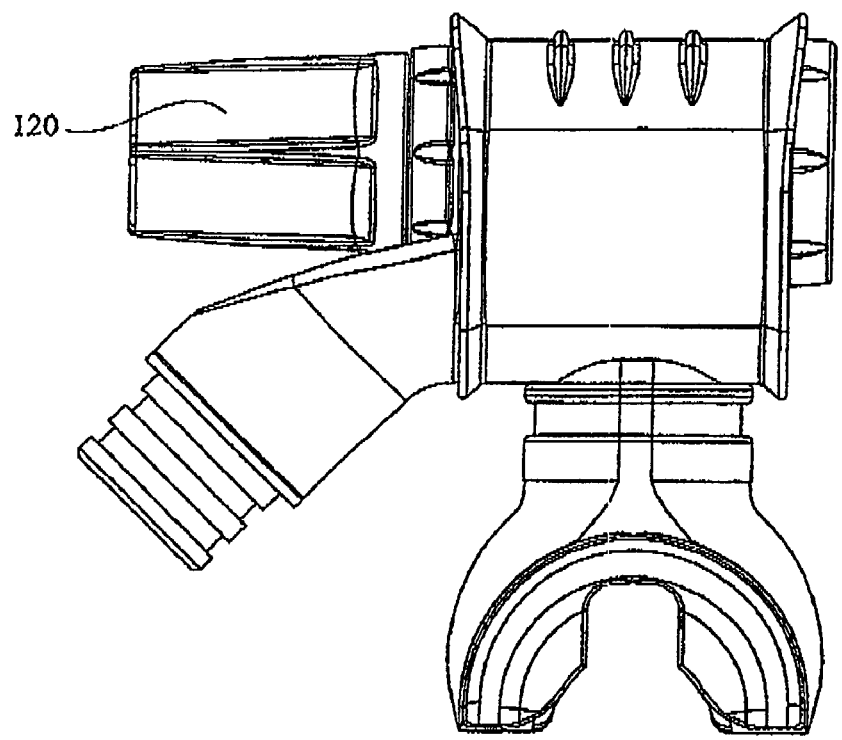
Figure 22:
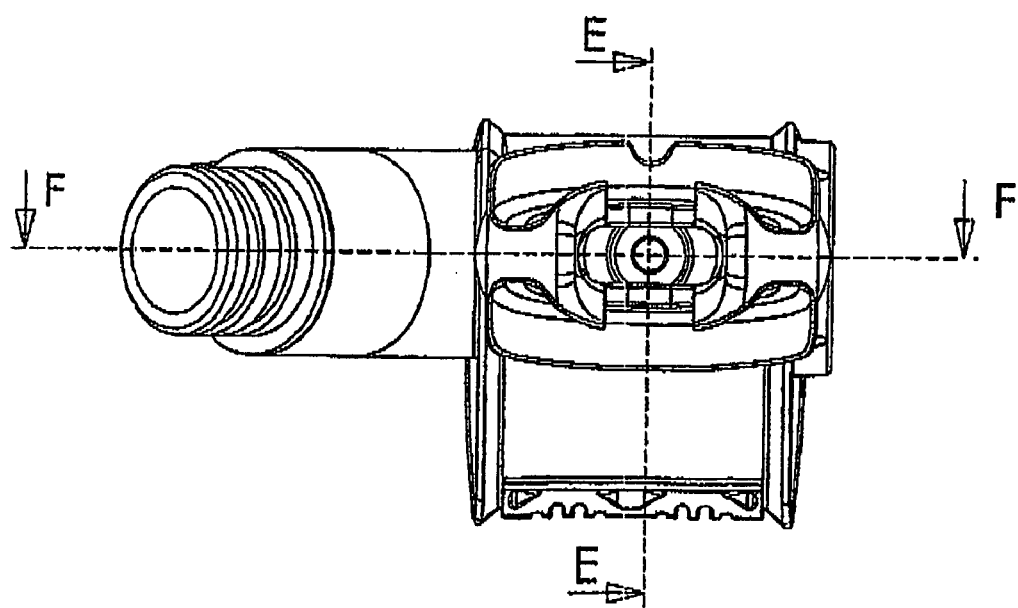
Figure 23:
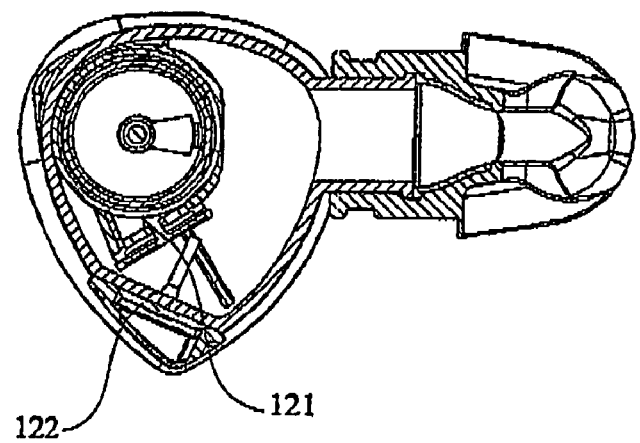
Figure 24:
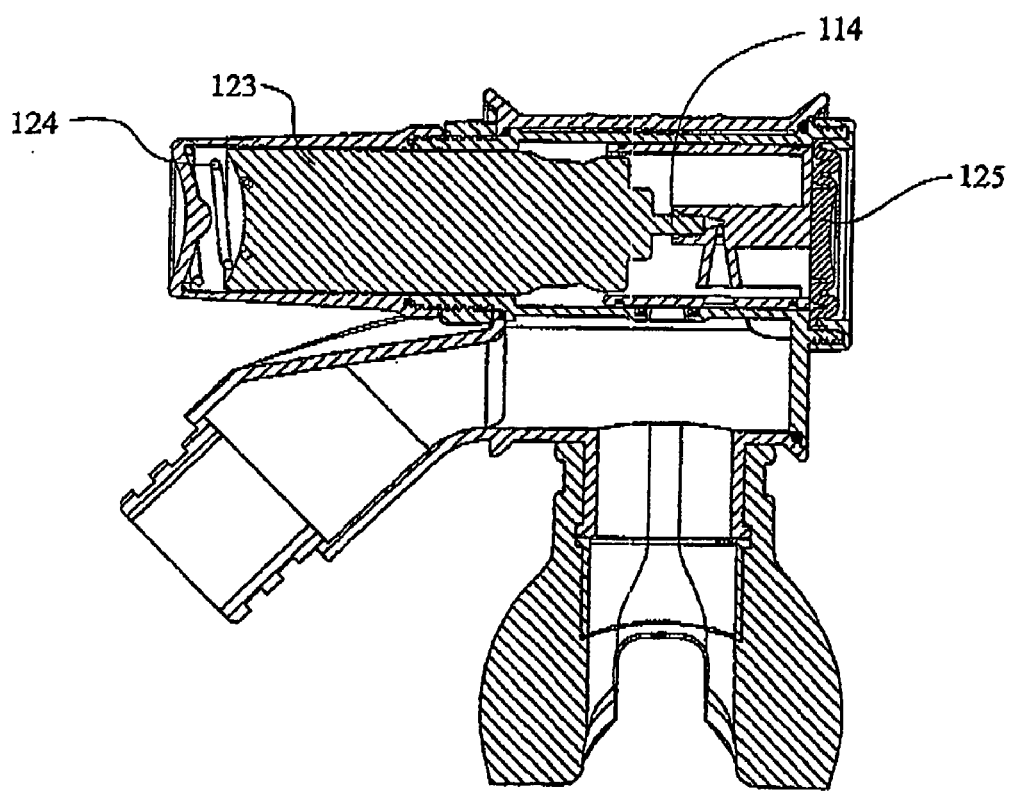

The internal structure is more readily discernible in FIG. 20. The hose mounting 103 provides a pathway 106 to the internal chamber 107 which in turn connects through the mouth piece spacer 108 to provide a pathway for inspired and expired air to the mouthpiece 101. A pressurised canister 109 is located in the medication chamber 104. The canister sits against an end cover 110. It is possible that the end cover would be displaceable to operate the pressurised canister but in this embodiment activation occurs at the other end. The external body 111 supports a slider housing 112 which in turn provides a path for the slider 113 which is formed as a piston. Pressure on an activation button 105 causes displacement of the nozzle 115 downwardly onto the canister and discharge of a metered dose through the delivery chute 116 which may include wall apertures 117 and 118. Depression of the nozzle 115 will lead to alignment of the delivery chute 116 and apertures 117, 118 to provide the delivery pathway. An X-ring seal 119 may be provided to resist water entering the nozzle area. A lock ring 195 is provided to maintain the relative position of the components.

In operation, a user depresses the activation button 105 which leads to displacement of the piston or slider 113 and activation of the canister. The end cover 110 may be removed for replacement of the canister 109.

A variety of O-ring seals are also provided to enhance resistance to inflow of water or other contaminants.

FIGS. 21 to 24 show a similar arrangement to that of FIGS. 16 to 20. However, the medication chamber 120 in this instance is provided with a purge valve 121 located and directed generally in the same direction as the main purge valve 122. Additionally, the canister 123 is less compact and is mounted on a spring 124. Depression of the activation button 126 will therefore lead to displacement of the entire canister 123 as well as the nozzle stem 114. After release of the activation button 125 the canister 123 will be urged back into its starting position by the spring 124.

While activation by a push button is shown, it is also clear that a twist end arrangement as previously described may be used with a snorkel.

Figure 25:
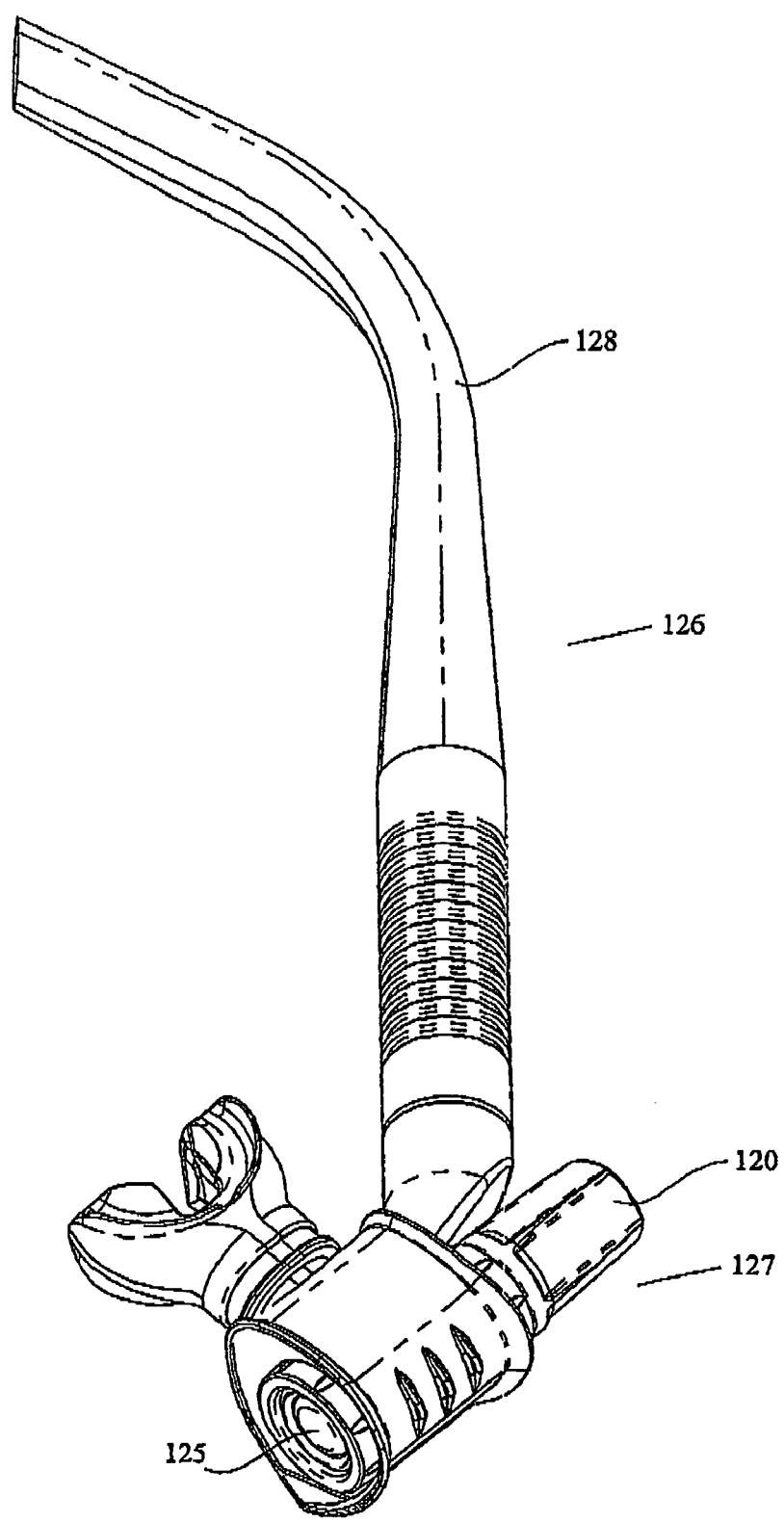

FIG. 25 shows a perspective view of an assembled modified snorkel 126 formed according to the embodiment of the base of FIGS. 21 to 24. The base 127 is engaged with a snorkel hose 128 to provide a fully assembled modified breathing apparatus. The medication chamber 120 may be removed for replacement of the internal canister. Activation of the button 125 will lead to dispensing of the required dose of medication.

Figure 26:
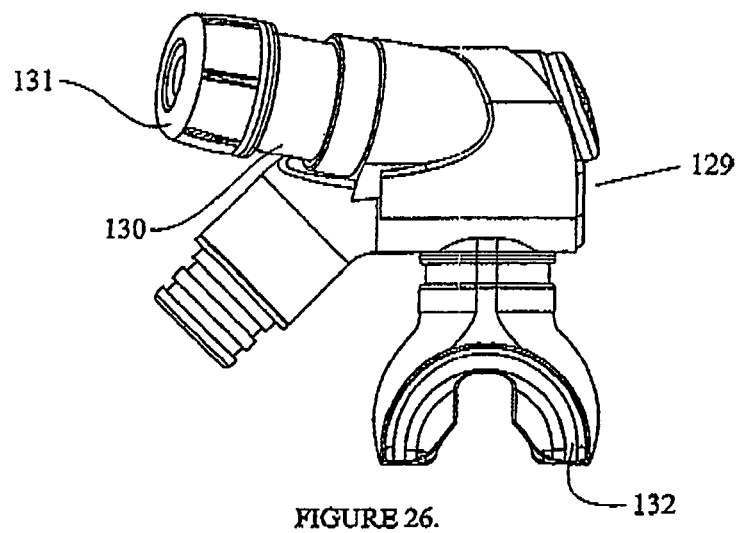
Figure 27:
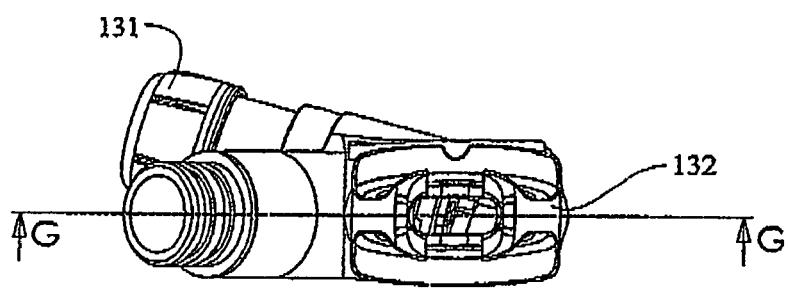

FIG. 26 shows an alternative snorkel base 129 in which the medication chamber 130 has a twist cap end 131 which may be rotated to provide displacement and activation of the canister internally. The twist cap end 131 activates a cammed device which leads to displacement of a piston in the cylinder of the medication chamber to a preset distance before return of the piston due to the cam advancing past an uppermost point and allowing the piston to reset in its original position. The rotating cammed edge is envisaged preferably as a saw tooth arrangement which allows dispensation of a dose with each 90° of rotation. This mechanism may be similar to that described earlier. However, different arrangements may be utilised. The preferred mouthpiece 132 is seen in FIGS. 26 and 27.

Figure 28:
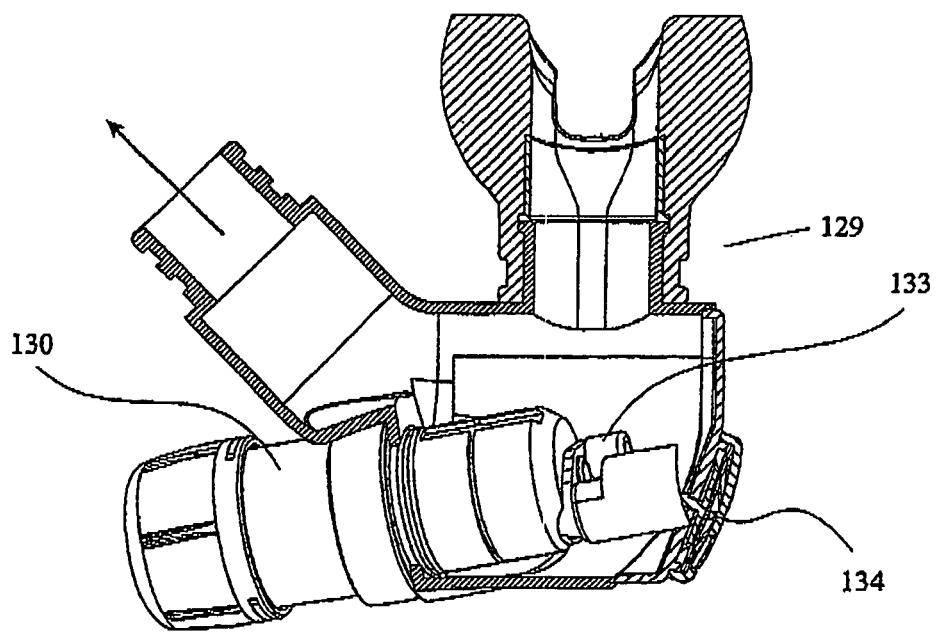

FIG. 28 is a sectional view which shows the medication chamber 130 positioned within the modified snorkel base 129. As noted above, in the preferred embodiment, the medication chamber is formed as a universal fitting which may be applied to a snorkel, a regulator or other breathing apparatus. When going from use in a regulator to use in a snorkel, a cover cap 133 may be usefully applied over the air inlet of the medication chamber which is adapted to connect to a pressurised air supply line. The cap is preferably adapted for easy placement on the air inlet or alternatively removal as required. The slight modification allows wide use of the medication chamber with different breathing arrangements.

A main purge valve 134 of the snorkel is also apparent in this view.

Figures 29, 30:
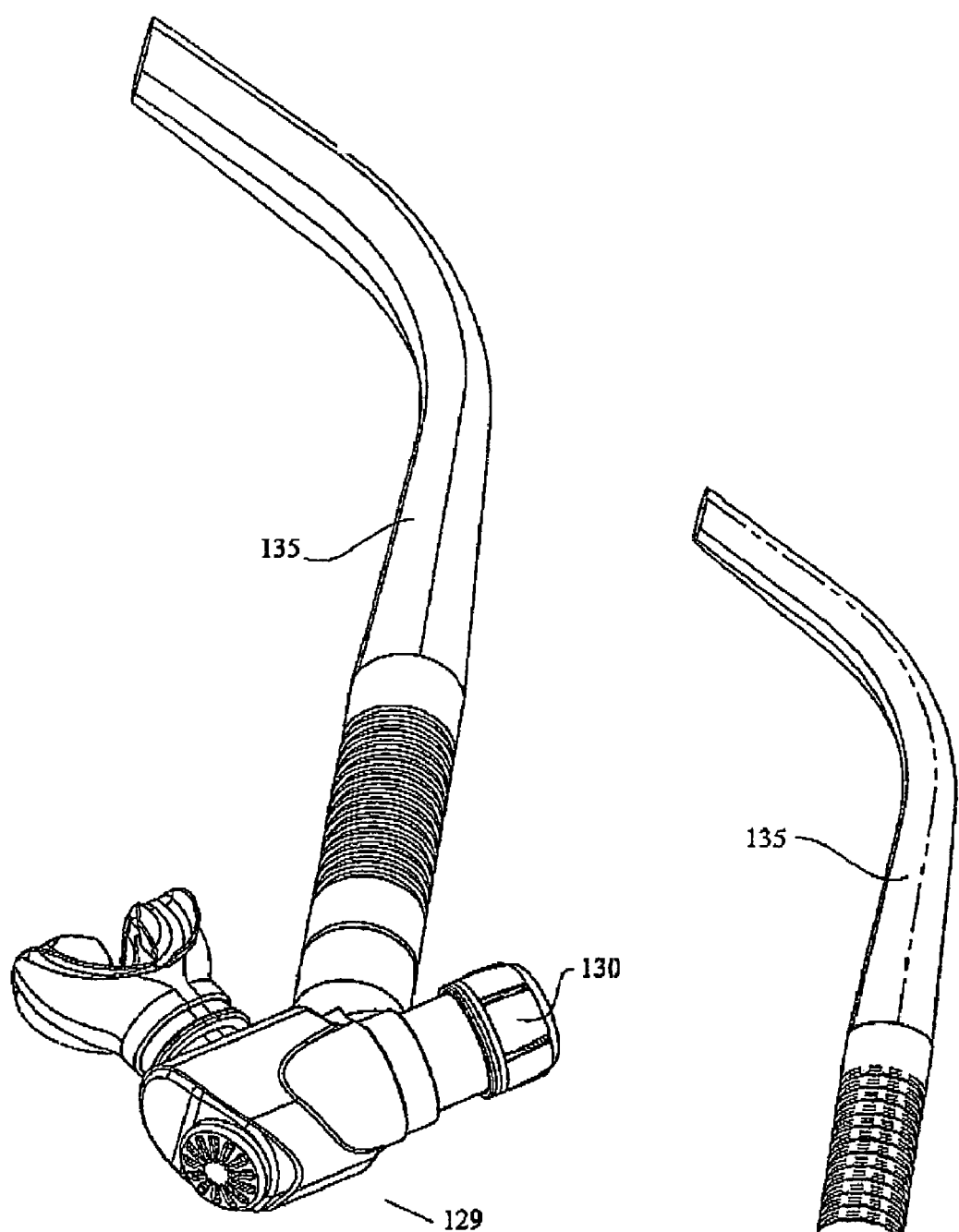

FIG. 29 shows the base 129 of FIG. 28 when connected to a snorkel hose 135 and with the medication chamber 130 in position. FIG. 30 shows the alternative arrangement with the medication chamber absent. A plug 136 may be inserted into the resulting cavity so that the snorkel is available for use without the medication chamber.

Figure 31:
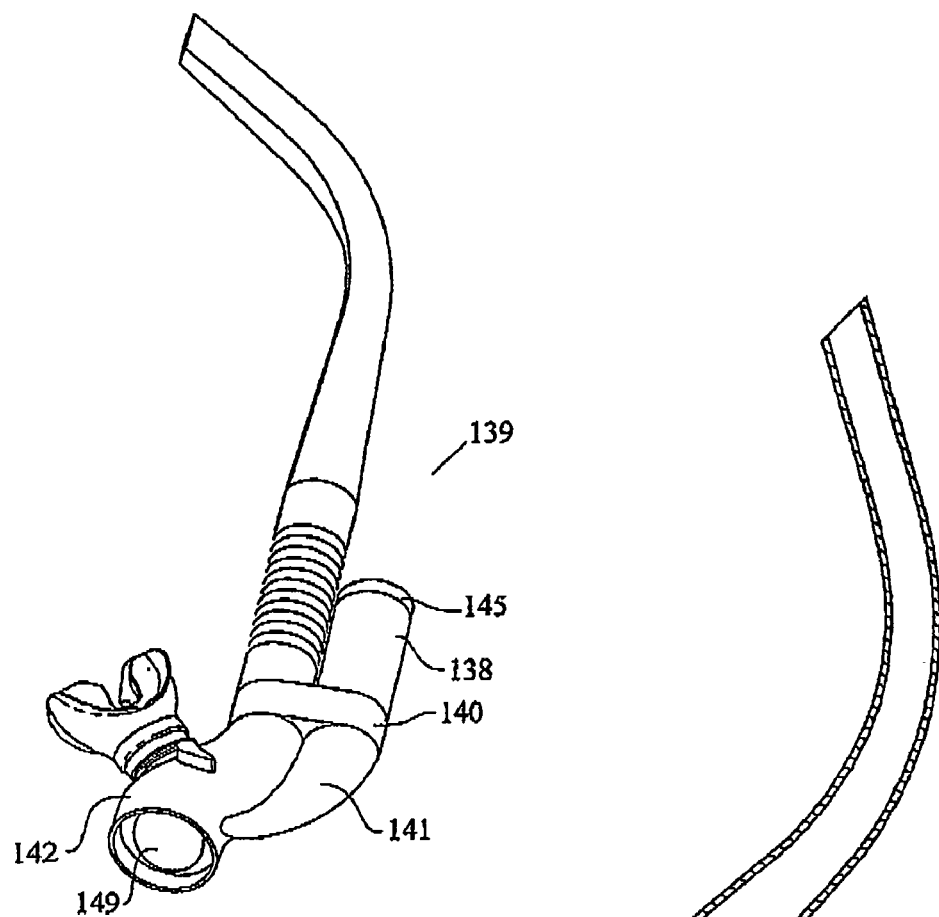
Figure 32:
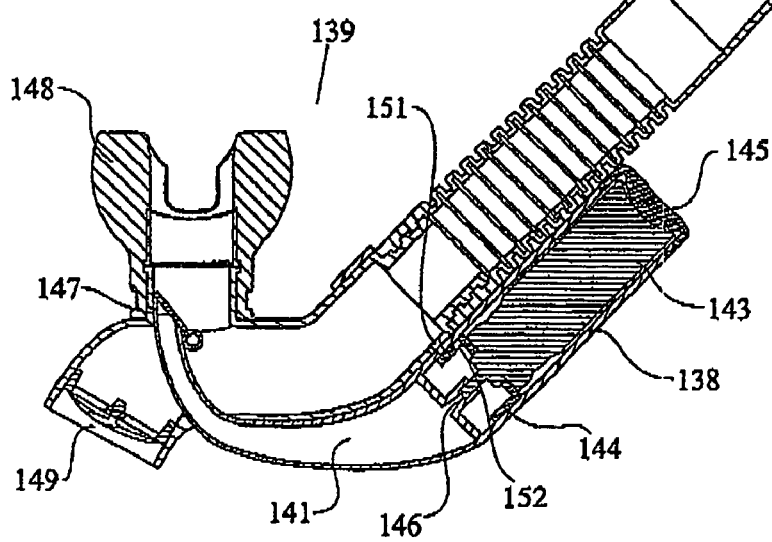

FIGS. 31 and 32 show a further alternative embodiment of a snorkel in which the medication chamber 138 is mounted to the snorkel 139 by a bracket 140 and includes a delivery chute 141 entering the snorkel base 142 towards its bottom.

The arrangement is seen in a sectional view in FIG. 32. The pressurised medication canister 143 is positioned against seat 144 and may be activated by depression of the activation button 145. Discharge through the nozzle 146 is dispensed into the chute 141. Pressurisation of the chute 141 causes displacement of the trap door 147 and presentation of the dose to the mouth piece 148. While such an operation is possible, it is envisaged a more positive operation would arise from manual operation of the trap door 147 through a digitally activated lever, knob or similar. A purge valve 149 is also apparent in this view. This embodiment provides a simple arrangement for medicating the air stream of a snorkel. The end cap 145 may be easily removed to provide access to the canister for replacement. It may be fixed to the chamber 138 by any suitable reasonably robust means such as by a screw fitting, resilient location in a receiving recess or other arrangement. Preferably the fitting is water tight.

Figure 33:
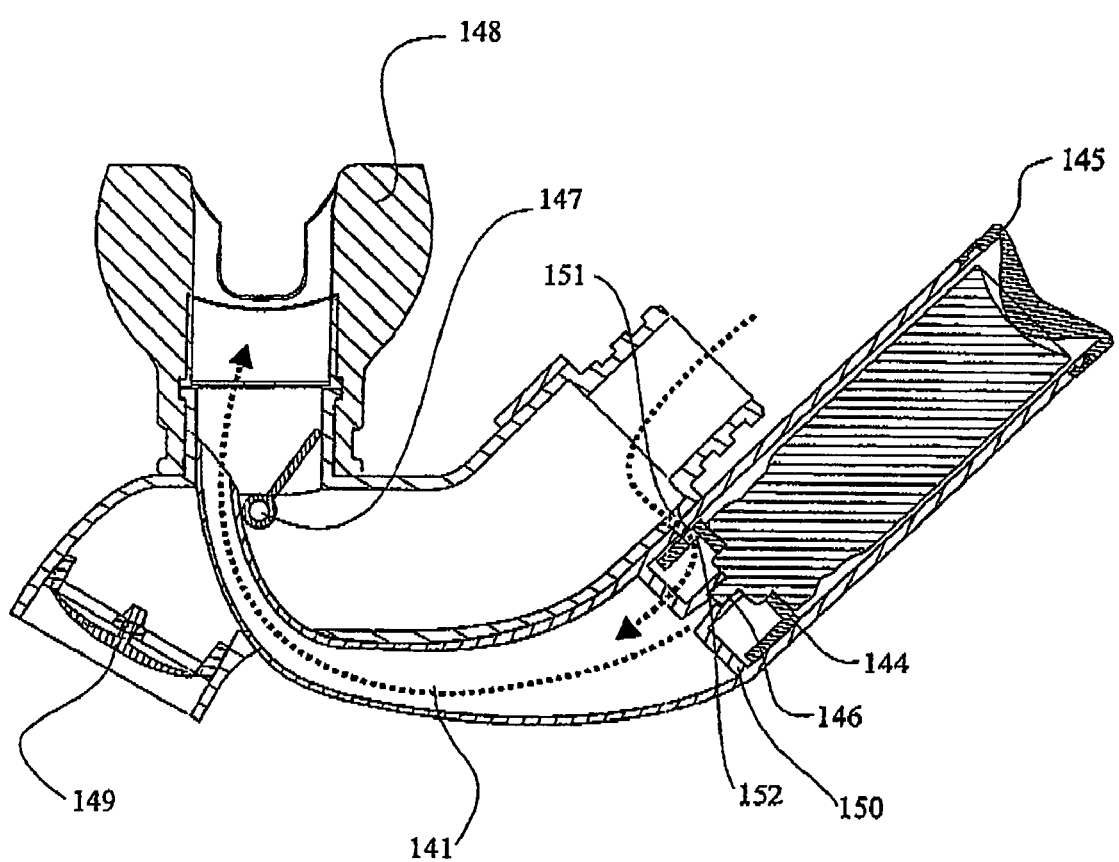

FIG. 33 shows the arrangement of FIG. 32 in operation. The activation button 145 is depressed causing the seat 144 to advance towards the wall 150 thereby also resulting in depression of the nozzle or valve stem 146 and discharge of a dose of medication. The flow valve or trap door 147 is opened by the pressurisation of the chute 141 or manual displacement and also serves the purpose of restricting the flow of air through the body of the snorkel to ensure uptake of the medicated dose. In this arrangement, depression of the canister will cause alignment of two small air flow apertures 151, 152 to provide an air flow through the chute to maximise displacement of the medicated dose towards the mouthpiece. Resulting air flow is indicated by dotted arrows. When inactive, the apertures are out of alignment and therefore closed as is apparent in FIG. 32.

Figure 34:
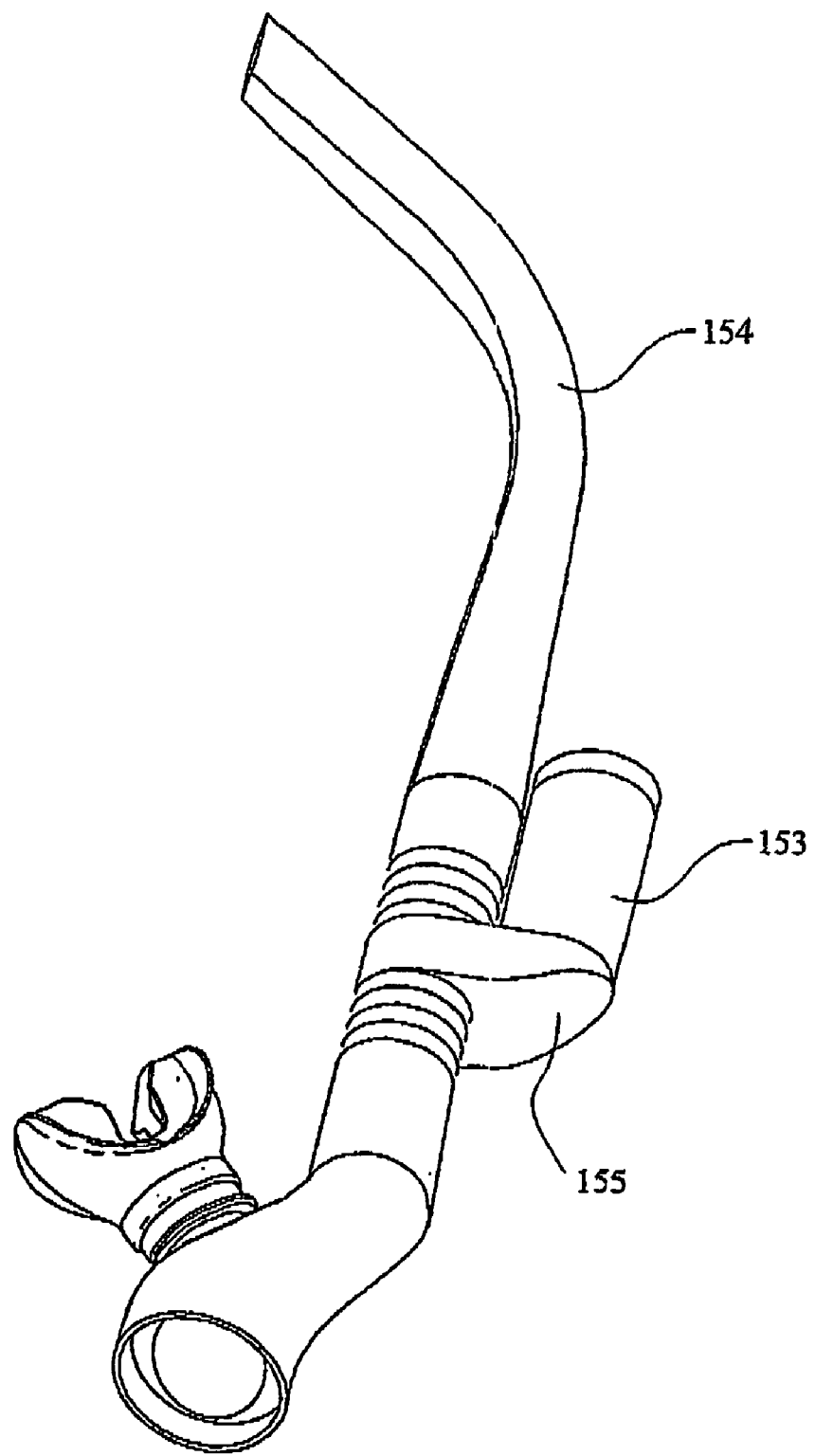
Figure 35:
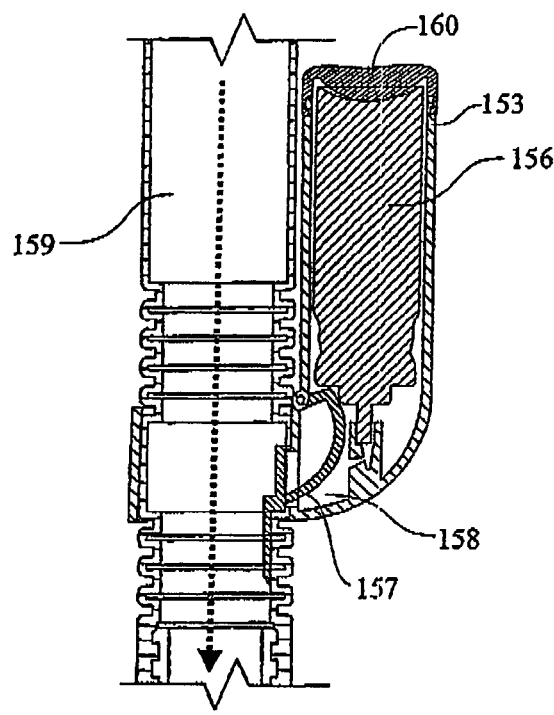

FIG. 34 shows a further arrangement for a snorkel in which the medication canister 153 is mounted some distance up the snorkel hose 154 on a bracket 155. The resting or inactive arrangement is seen in FIG. 35 in which the canister 156 is located in the chamber 153 and rotatable door 157 seals the chute section 158 of the canister from the main air passage way 159.

Air flow is indicated by the dotted arrow and entirely through the main snorkel passage 159.

Figure 36:
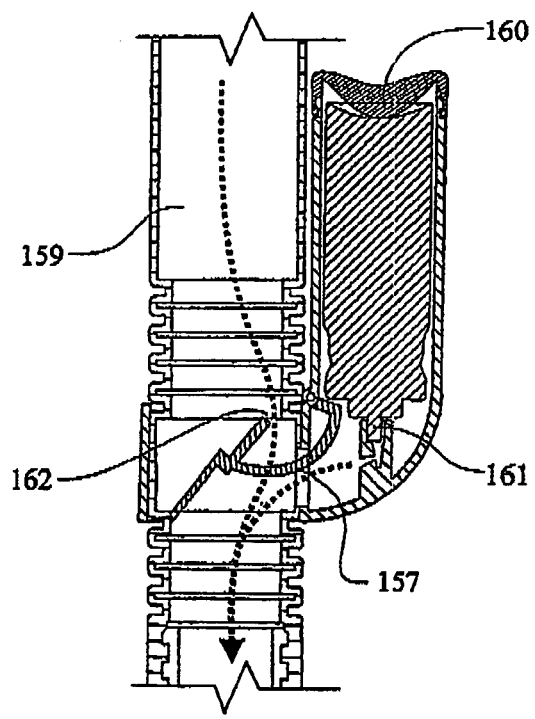

In FIG. 36, the activation button 160 has been depressed causing depression of the valve nozzle 161 and also leading to rotation of the door 157 by contact with a shoulder of the canister resulting in a patent channel into the main air passageway 159. Displacement of the door also reduces airflow from the main channel 159 and thereby increases delivery effectiveness to a user.

The door includes an aperture 162 to avoid occlusion of the main passage way. The dotted lines indicate the direction of air flow and medication dispersal.

Figure 37:
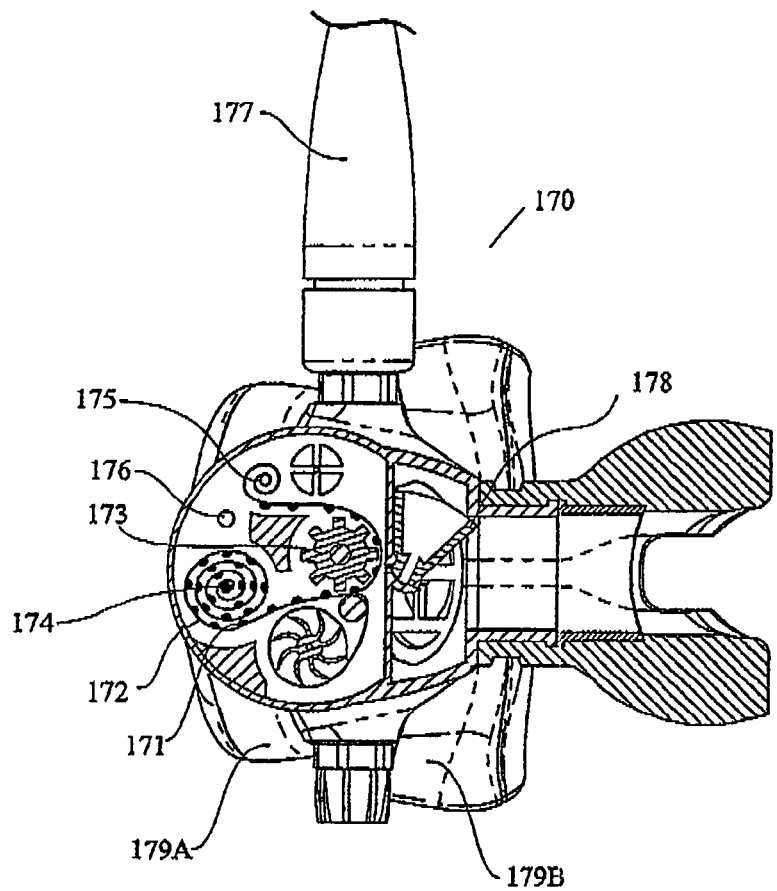
Figure 38:
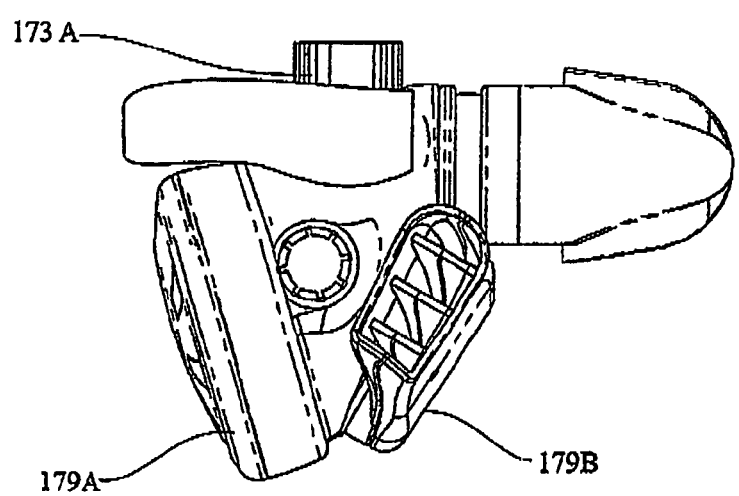
Figure 39:
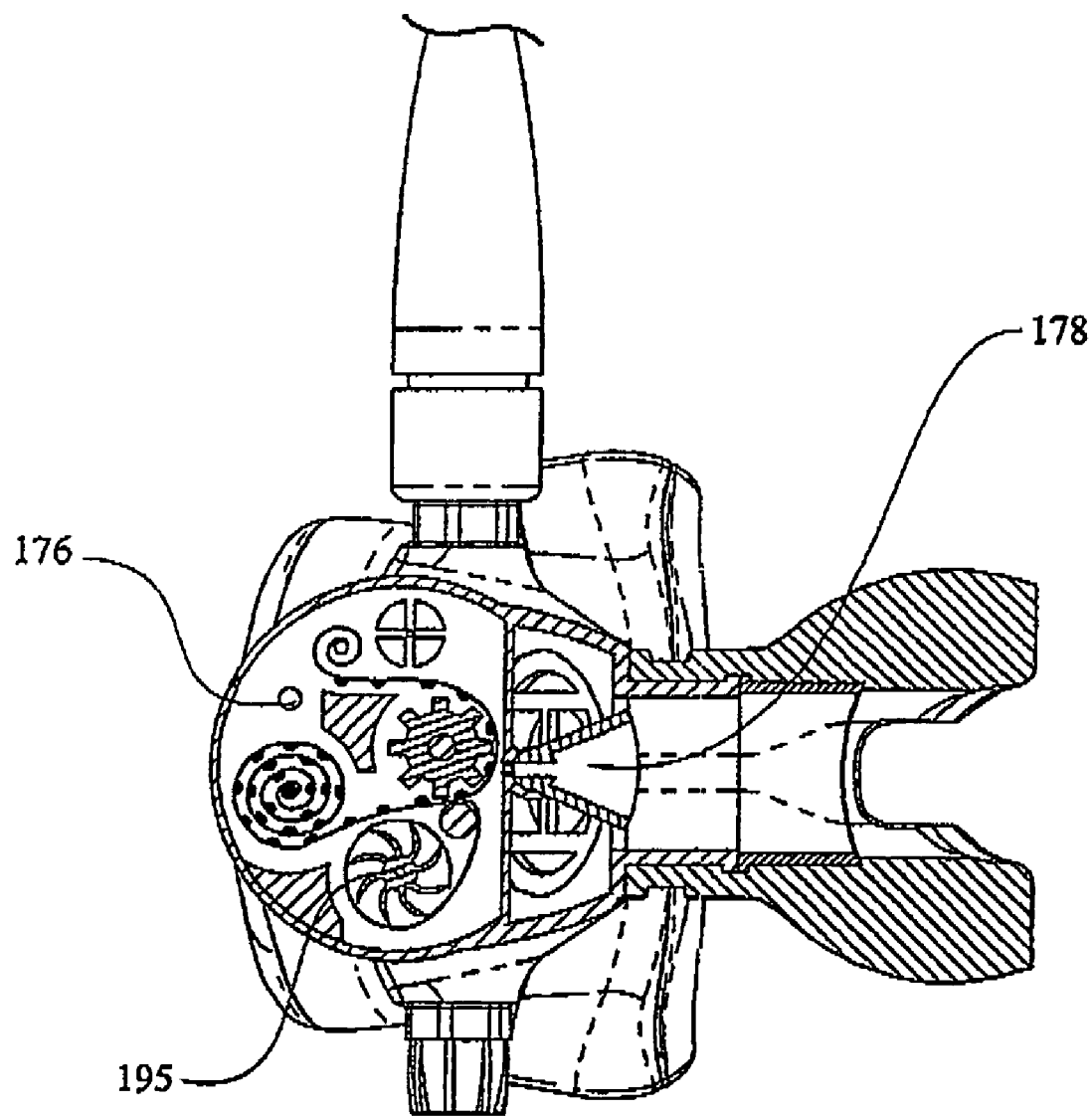
Figure 40:
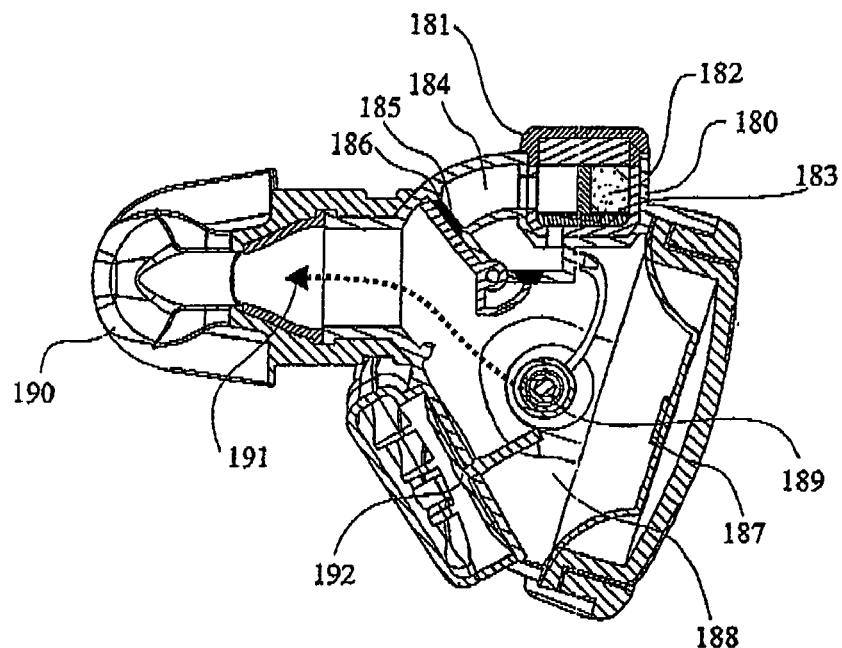
Figure 41:
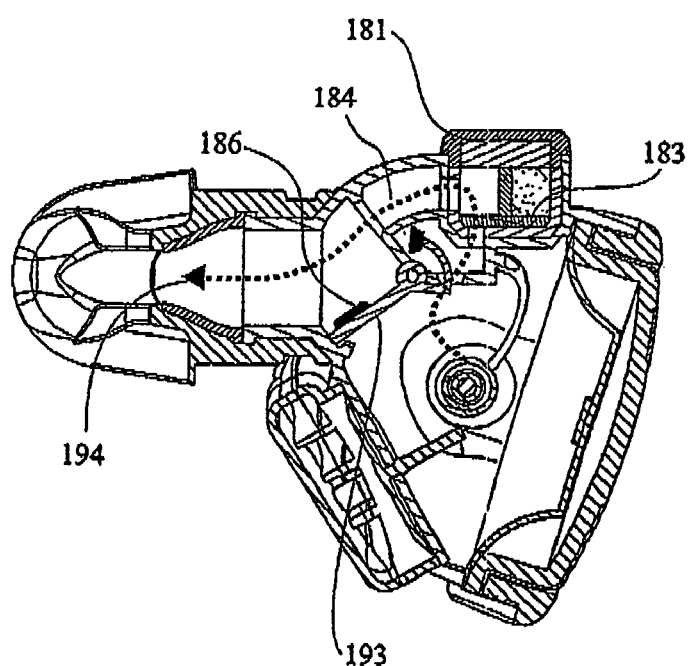
Figure 42:
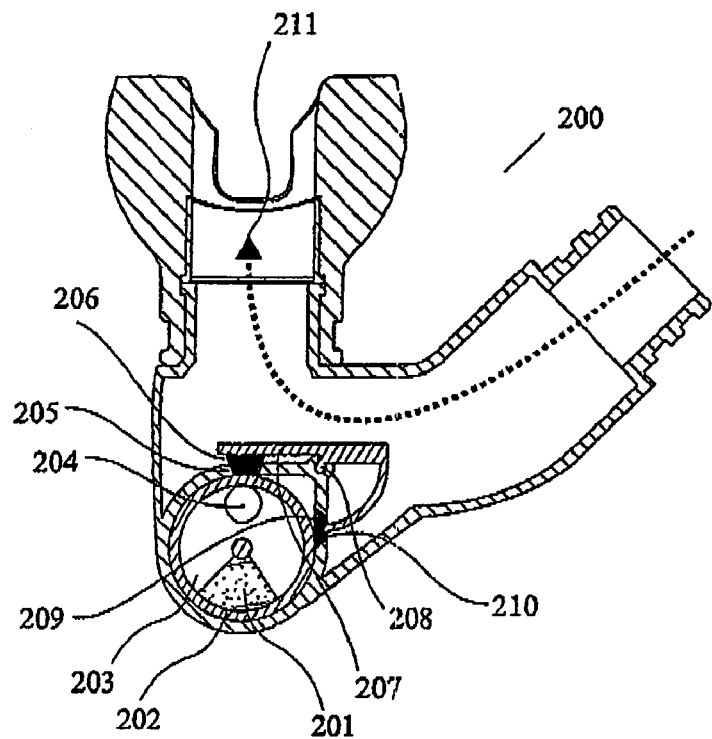
Figure 43:
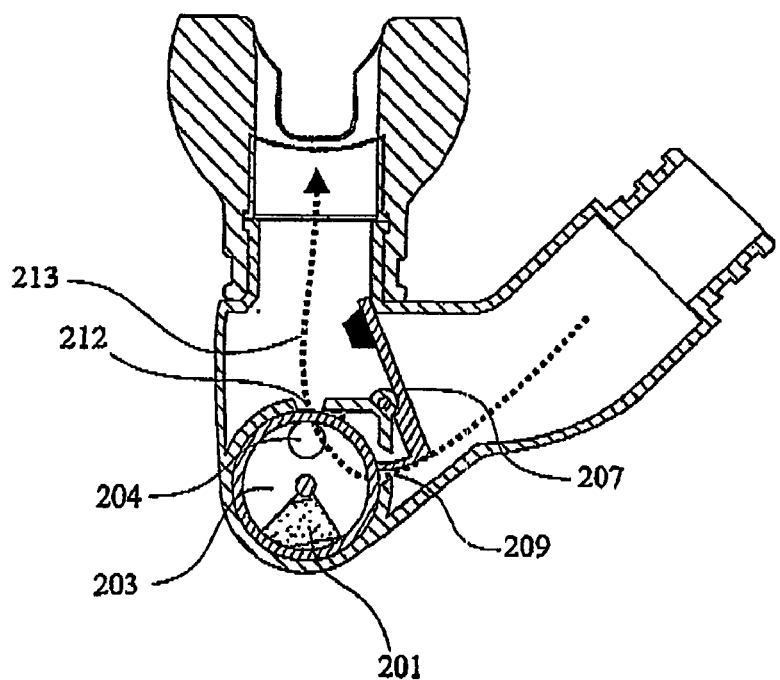
FIG. 43 shows the arrangement of FIG. 42 in operation.
Figure 44:
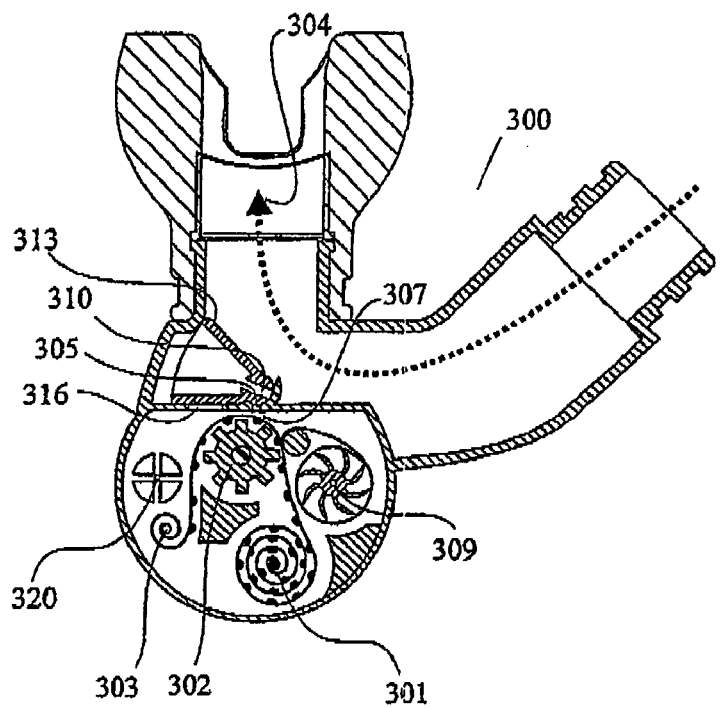
FIG. 44 is a sectional view of a further arrangement for use of dry powder with a snorkel when using blister packs.
Figure 45:
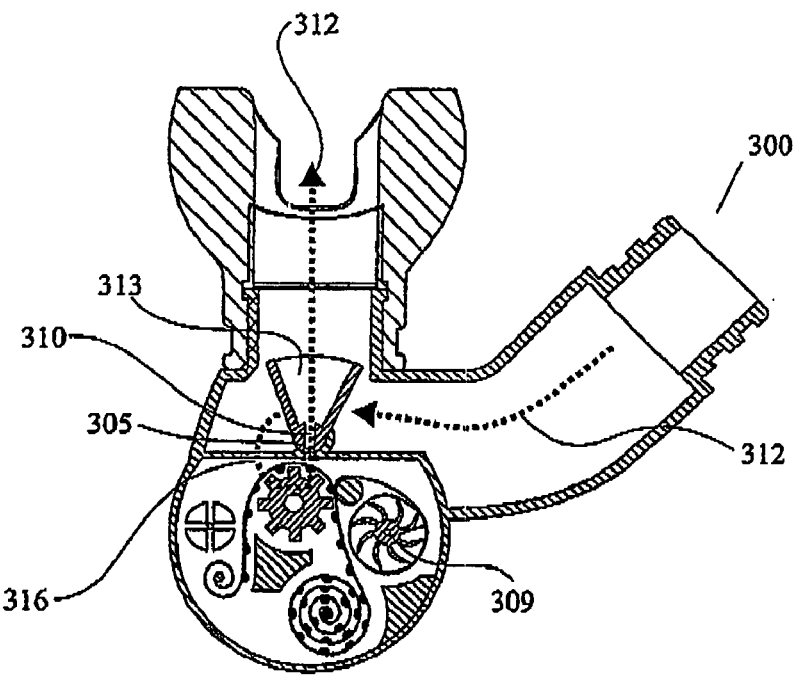
FIG. 45 shows the arrangement of FIG. 44 in use.

FIG. 37 shows an arrangement for a modified regulator 170 when using a dry powder held in blister packs 171 laid on a roll 172. A twist top is provided to activate the cog 173. Drive to the cog 173 advances the roll 172 from holding spool 174 and it is wrapped onto receiving spool 175. The air inlet 176 is provided for introduction of the air from delivery line 177. A standard operating regulator diaphragm 179A and purge exhaust valves 179B are also provided. FIG. 38 shows the twist top 173A in side view. An inhalation tunnel 178 is rotatable between a stowed position (FIG. 37) and a dispersing position (FIG. 39). In the stowed position, the delivery pathway for medicating the airstream is occluded. Movement to the dispersing position opens the air pathway.

In FIG. 39 the inhalation funnel 178, which was stowed in FIG. 37 is now positioned and when turned into place drives the geared assembly for the advancement of the blister strip and its rupture to dispense the powder into the air passageway through the inhalation funnel. The air inlet 176 provides equalisation of the pressure between the medication chamber and the regulator body. A secondary spool 195 may also be provided to receive the stripped plastic coating from the pack. An impeller (not shown) may be used to disperse powder dispensed upstream from the impeller for subsequent suction through and dispersal by its action.

An alternative arrangement for use with a regulator and dry powder is seen in FIG. 40. The chamber 180 is provided with a twist top 181 which when activated will provide dry powder medication 182 to a dispensing disc 183. The disc in operation communicates with delivery chute 184 which terminates in a medication outlet 185 which when not in use is closed by a valve 186.

When non-activated a standard operation regulator diaphragm 187 controls inlet of air into the chamber 188. Respiratory air is provided through air inlet 189 and is transported to the mouthpiece 190 in standard flow according to arrow 191, during inhalation. A purge valve 192 leading into an exhaust vent are apparent.

In FIG. 41 rotation of the twist top 181 has opened the valve 186 which is supported on door 193 and created an air pathway demonstrated by arrow 194. The doorway 193 partially occludes the ordinary air flow passage way and directs air through the delivery chute 184 thereby leading to flow through the disc 183 and dispersal of the powder medication. The disc may be formed with a sieve-like base to permit flow of air through the powder with subsequent entrainment. The chamber 180 may be formed integrally with the body of the regulator. Alternatively, it may be formed as a drop-in modular component lockable in position with any suitable arrangement.

A dry powder arrangement for a snorkel is shown in FIG. 42 wherein a snorkel bore 200 is provided having a dry powder medication 201 in a chamber 202. A rotating disc 203 is provided which when activated will present a measured dose of dry powder to an inhalation area 204. A medication outlet 205 is closed by a valve 206 supported on a rotatable flap 207 which in turn is pivoted on pivot point 208. An air inlet 209 is also occluded by a secondary valve 210. An ordinary air pathway is shown by arrow 211.

Operation of the arrangement is shown in FIG. 43 where the flap 207 is pivoted open, and partially occludes the ordinary air pathway and creates an air inlet 209 and exit 212 allowing the flow of air according to arrow 213. Rotation also causes the disc 203 to present a dose of powder 201 to inhalation area 204 for subsequent entrainment in the air stream and delivery to a user. The disc is formed with a scoop or spoon section for capturing a predetermined amount of the medication material.

A blister pack arrangement for a snorkel is seen in FIG. 44. A modified snorkel base 300 is provided having a feed spool 301, a drive cog 302 and receiving spool 303. In resting use, air is provided through air pathway 304. A delivery chute 313 is rotated into a stored position and the medication outlet 310 is closed due to non-alignment with aperture 305 and inhalation area 307 due to rotation of the chute 313. An activation button (not shown) may be spring loaded to an inactive position. A blister pack is ruptured and powder presented to the inhalation area 307 when the button is activated. Stripped plastic coating is loaded onto a receiving spool 309.

In FIG. 45 the activation button has been depressed leading to rotation of the chute 313 and alignment of the inhalation area 307, aperture 305 and outlet 310 thereby creating an air pathway. A second aperture 316 provides an air inlet once cleared by rotation of chute 313 pathway as seen in FIG. 45 to allow air to flow along direction of arrow 312. This provides dispersal of the powder into the air stream for discharge through the medication outlet 305 and channel 310.

FIG. 46 shows a front view of a dosage device or modified breathing apparatus 510 of the present invention. A primary air line 511 provides a pathway for air 512 or air mixture originating from the pressurised tank on a divers back. The primary airline 511 terminates in a demand valve 513 which operates in the standard way for delivering pressurised air into the second stage chamber 514 which is shown drawn only in part having partial side walls 515, 516.

A bifurcation results in secondary line 517 which provides compressed feed air to the dosage device 510 of the present invention. It is understood that reference to compressed air includes reference to any appropriate compressed gas or gas mixture including oxygen nitrogen combinations such as NITROX and other gaseous combinations. Modified breathing apparatus 510 comprises an outer housing 518 which may be formed from any suitable non-flexible material such as metal or polymer. A drug container canister 519 is positioned in an internal chamber 520 of the modified breathing apparatus.

It is envisaged that the canister 519 will contain a pressurised quantity of therapeutic agent or other form of physiologically or mechanically active substance with a discharge mechanism that is pressure activated. The canister 519 is mounted on two ledges 521 and compressed in place by a suitable packing material such as a tension foil 522. The canister 519 has two outlet apertures 523, 524 which are urged into close proximity and sealed engagement with the discharge bore. When not in use the apertures are urged against a lock slide 525 which may be formed with a security seal 526, the purpose of which is indicated when the device has been operated thereby indicating to an overseeing diving instructor, health professional or other suitable party such as a service or technical agent that the canister may be depleted. In a preferred operation it is envisaged that the canister will be a one use item which may include a number of activations of the device which is disposed of after any single dive in which the device is operated. The lock slide 525 has two through bores 527 which are usually out of alignment with the outlet apertures 523, 524. However, when the device is to be used a rotatable lock screw 528 may be released providing the ability to slide lock slide 525 to a position where the through bores 527 and outlet apertures 523, 524 are in corresponding alignment thereby providing a pathway from the outlet apertures through the through bores and into flow channels 529, 530 directed towards the air stream in the chamber 514 and for inhalation through the mouth piece (not shown). The slide is preferably sealed to prevent ingress of water. O-ring seals may be appropriately located to provide this function. Further the canister apertures 523, 524 may be adapted to sealingly engage the slide rod when the through bores 527 are aligned. O-rings may again be suitable for the purpose.

The present device has an internal chamber 520 which is equalised with ambient water pressure through the demand valve 531 and demand valve lever 632. If the pressure in internal chamber 520 drops below ambient water pressure, the balance diaphragm 533 expands urging the demand valve lever 532 out of its resting position and thereby unseating a valve to allow inlet of air at high pressure into the chamber 520. Should the pressure in the chamber 520 exceed ambient water pressure, air may be discharge through exhaust valve 534. The exhaust valve release pressure of the chamber may be set slightly higher than ambient pressure (ie. increased activation pressure differential required) or the demand lever may be adapted to activate at an increased pressure differential so that the chamber is generally slightly blow ambient pressure. The internal chamber 520 is protected by a chamber seat 535 which abuts a spacer 536 which is in itself in contact with a rubber cover 537. This view also shows an exhaust tube for discharge gas from primary and internal chambers 538.

In operation therefore, a diver will breathe as usual in a scuba diving arrangement. Should the diver find themselves requiring medication, they will simply unlock the look slide 625 by rotation of the lock screw 528 and slide the lock slide 525 outwards thereby breaking the seal 526. The lock slide may be fitted with a slide location pin 539 for fixing the lock slide in operating position. Once a pathway is provided between the canister apertures 523, 524 and the flow channels 529, 530 an operator pushes on the rubber cover 537 which leads to depression of the spacer 536 and seal 535 and subsequent pressure on the canister 519 leading to activation of the normal discharge aerosol valve as is well known in medihalers such as Ventolin® and Becotitde®. The appropriate number of depressions may be applied to medicate the diver. On completion, the lock slide 525 may be urged back to its original position and the lock screw 528 may be located into locked position.

Figure 46:
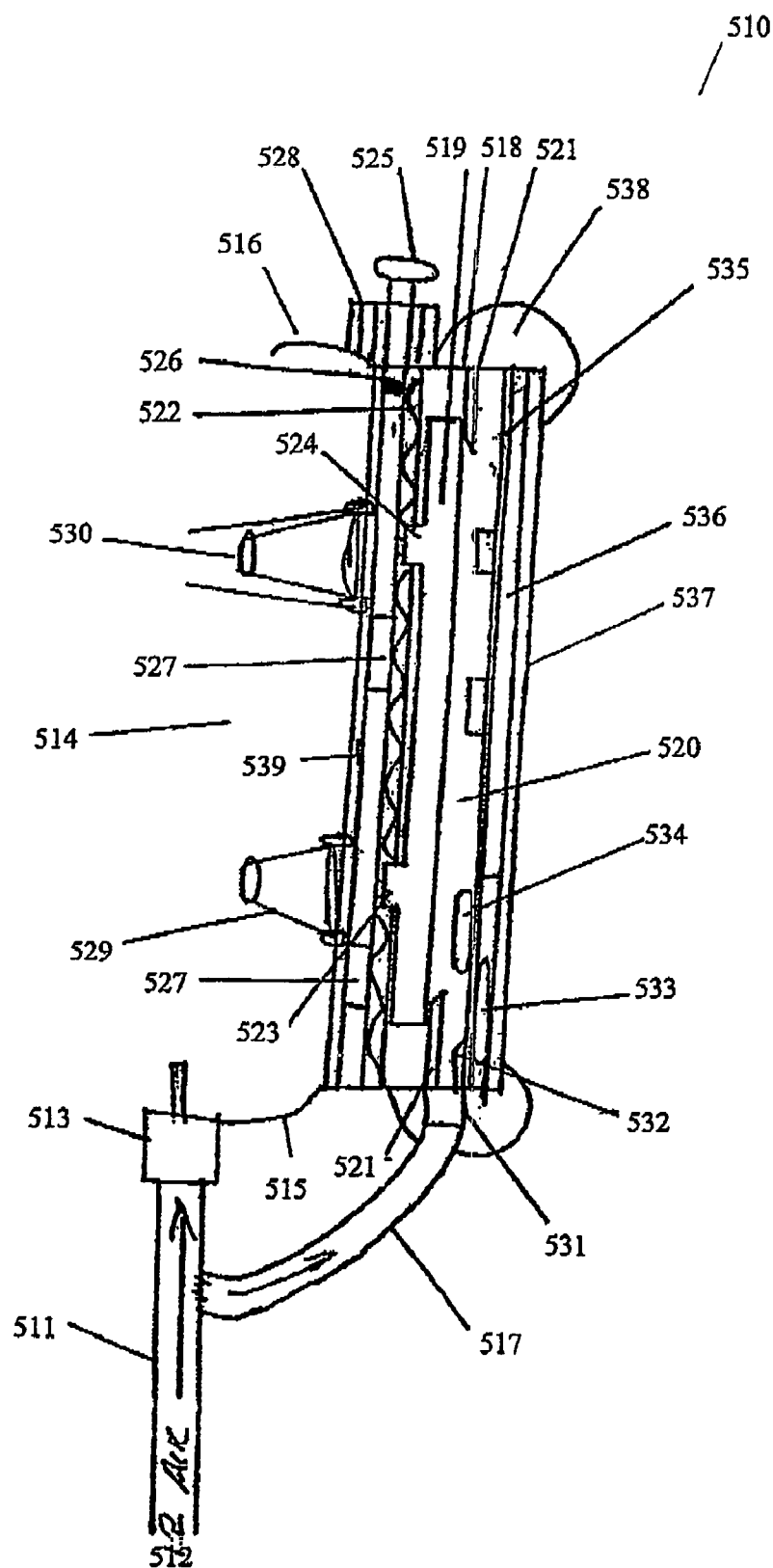
FIG. 46 is a part sectional top view of an alternative embodiment of a modified regulator.
Figure 47:
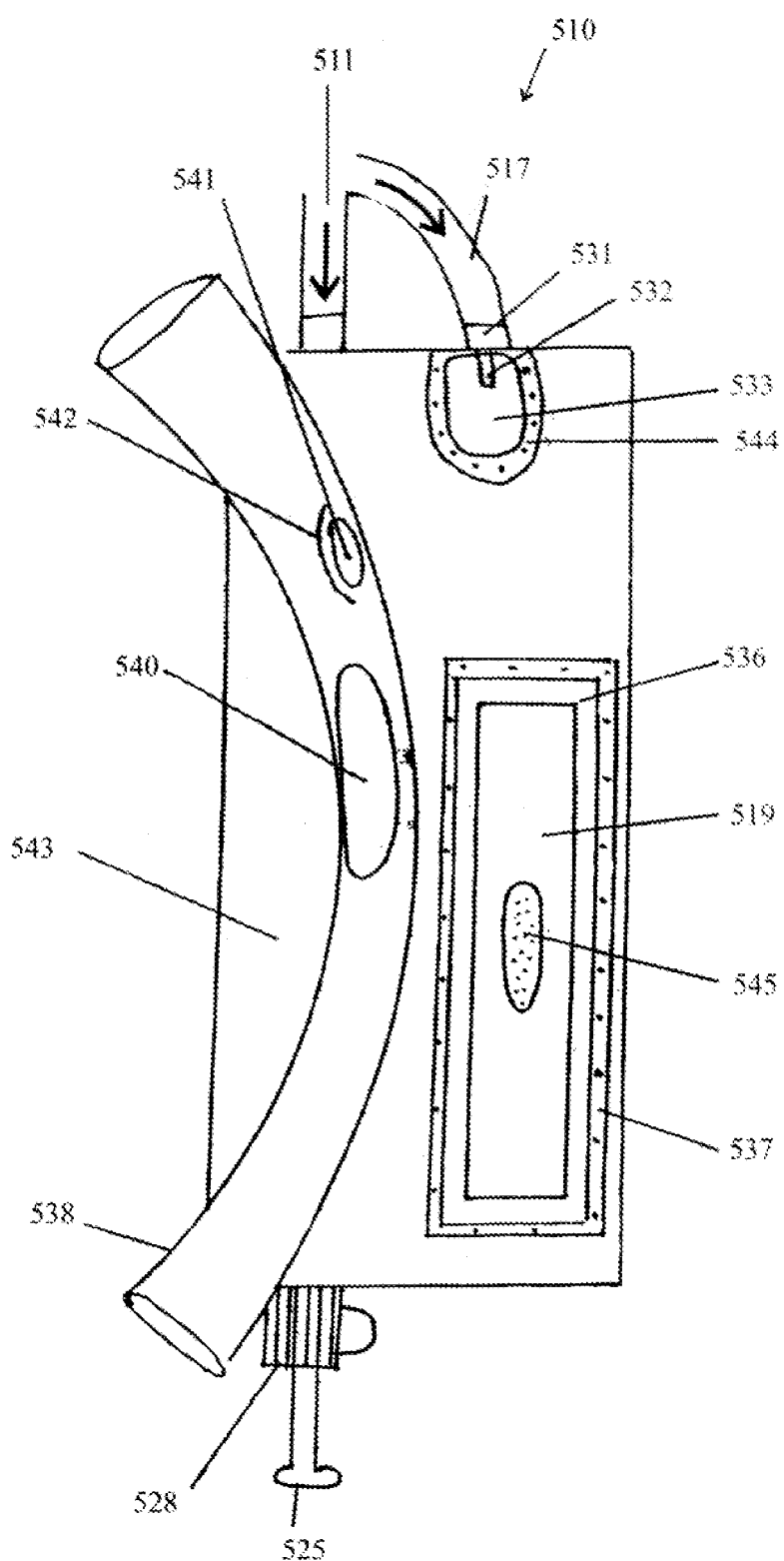
FIG. 47 is a bottom view of the arrangement of FIG. 46.

FIG. 47 shows a bottom view of the arrangement of FIG. 46 with the exhaust line 538 readily apparent as is the primary exhaust valve 540 which is slightly spaced from medication chamber exhaust 541 having a medication chamber exhaust cover 542. The side wall 543 of the primary regulator chamber is also visible as are the primary air line 511 and chamber air line 517 terminating in demand valve 531 and lever 532. The balance diaphragm 533 is visible in close proximity to purge cover 544. The slide 525 and slide lock 528 are provided. Rubber cover 537 is apparent and may have a ridged thumb grip 545. A diaphragm seal is located and outlines medical canister 519 which is shown as visible but may in fact be located behind the outer material.

The present device is suitably adapted for one handed operation by a diver. The hand may grip the chamber wall 543 with a thumb located over thumb operation pad 545 after having released the lock nut 528 and slid lock slide 525 into channel defining location. The canister 519 may be compressed by the thumb the appropriate number of times as indicated by the manufacturer or in keeping with the advice of a medical professional.

Figure 48:
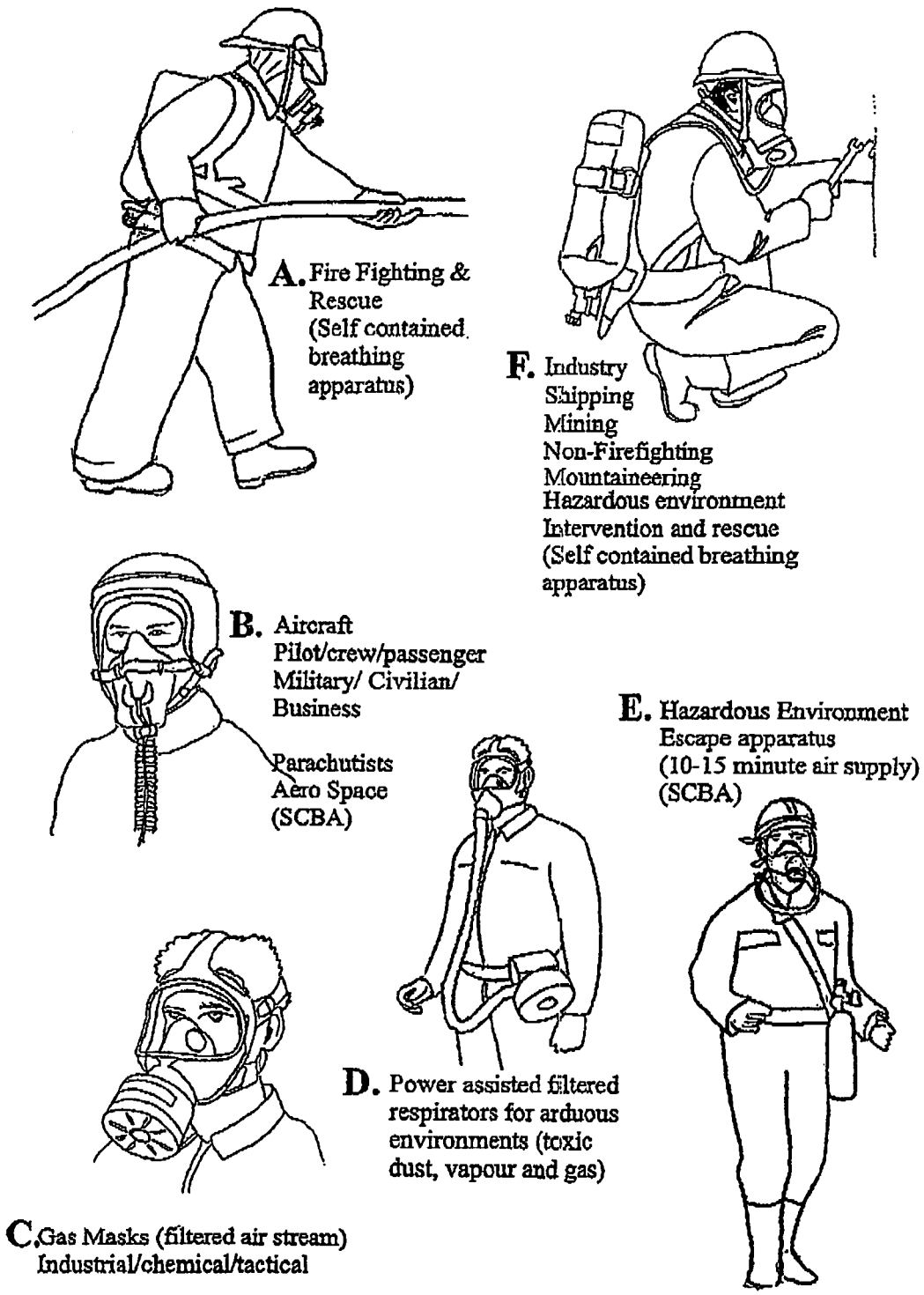
FIG. 48 shows a range of alternative applications of the present invention.

While the present invention is particularly well suited for snorkels and scuba regulators, the applications are far broader. Some representative applications are shown in FIG. 48 and include use by a firefighting officer 48A. The modified breathing apparatus of the present invention may also be suitable for use by pilots 48B and in gas masks where passive filtering of air occurs 48C. The device may be used in industries such as shipping and mining for self contained breathing apparatus 48F and in mountaineering. Use in hazardous environments and in escape apparatus 48E may be of particular assistance. The device may also be used in power assisted filtered respirators 48D for arduous environments.

Figure 49:
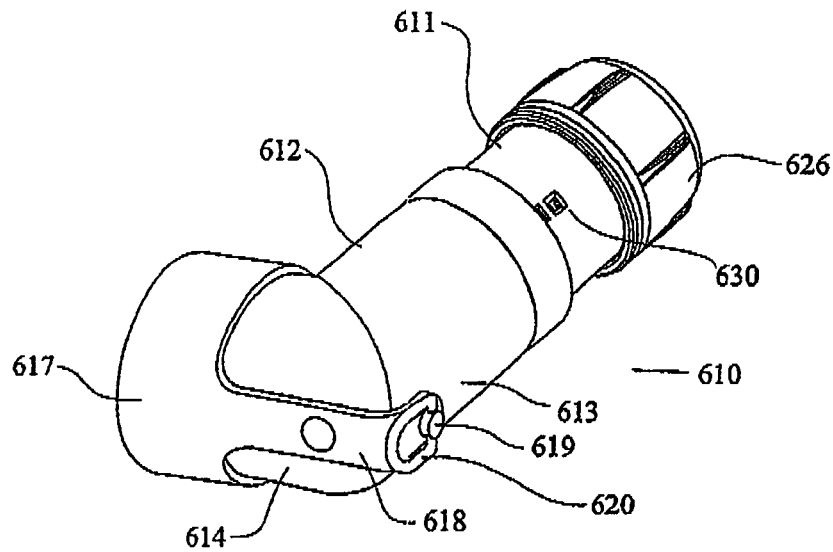
FIG. 49 is a perspective view of a removable medication chamber fixed to an alternative breathing apparatus.
Figure 50:
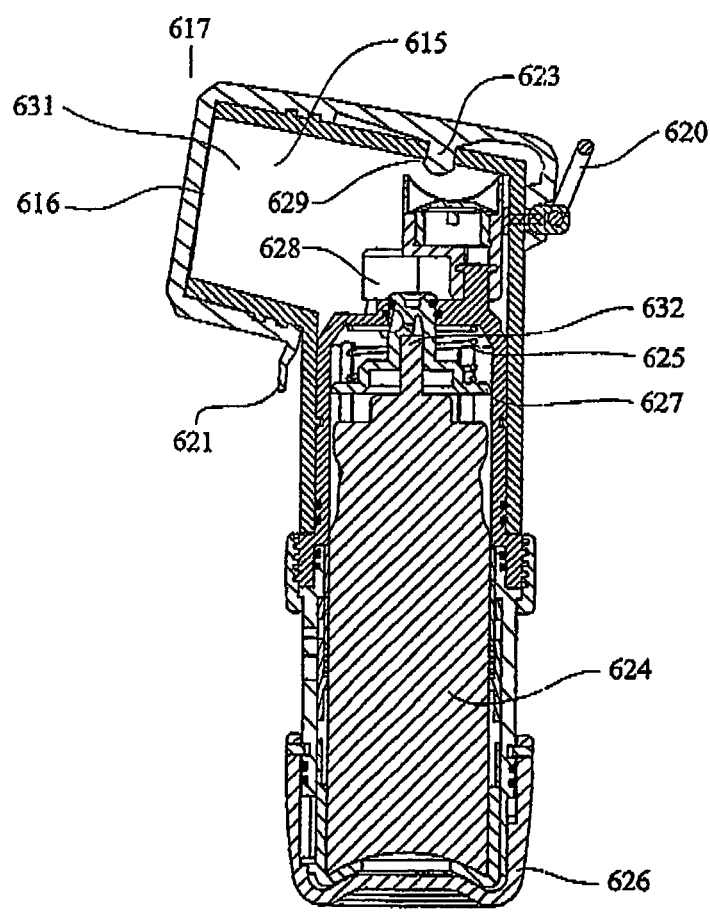
FIG. 50 is a sectional side view of the device of FIG. 49.

FIG. 49 shows a breathing apparatus 610 comprising a medication chamber 611 and breathing apparatus formed by breathing conduit 612. The conduit 612 is formed as an angularly deviating body with a central channel. A first segment 613 of the conduit 612 is configured to receive the medication chamber 611.

A second segment 614 deviates approximately 100 degrees from the first segment and has a medication delivery chute 615 with an outlet 616 adapted for location in the mouth of a user.

A removable cap 617 is positioned over the outlet 616 and a portion of the second segment 614. It is held in place by a resilient tie 618 which is fixed to a stud 619 on the first segment 613. The apparatus may include a loop 620 for receiving a tethering line or similar.

A tab 621 is available for finger activation to lift the cap 617 off the outlet and rotate it clear for use. This will also remove a plug 623 from an aperture 624 in the second segment 614 thereby creating an air flow pathway. A user may place the outlet in their mouth, close their lips around the second segment 614 and have an air inlet pathway through the aperture 629 and outlet 616.

The medication chamber 611 contains a medication canister 624 which is spring loaded into a resting position by internal spring 625. Rotation of the end cap 626 causes displacement of the canister as previously described and discharge through the valve stem 632 after compression against the seat 627. Discharge medication exits through the channel 628 and into the chute 631 for subsequent inhalation, The medication chamber 611 also includes a dose counter 630 as previously described.

The reference to any prior art in this specification is not, and should not be taken as, an acknowledgment or any form of suggestion that that prior art forms part of the common general knowledge in any country.

Throughout the specification, the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the disclosure.

The invention claimed is:

1. A modified breathing apparatus for medicating an air stream, said modified breathing apparatus comprising:
   a) a breathing apparatus including a regulator suitable for delivering air from a source of compressed air, the regulator adapted for use in at least one of scuba gear, aircraft applications, gas masks, hazardous environments, mountaineering, power assisted respirators, and a self-contained breathing apparatus;
   b) a medication chamber adapted to store and discharge a therapeutic agent;
   c) a delivery pathway between the chamber and an intake air pathway of the breathing apparatus; and
   d) a releasing means for selectively discharging the therapeutic agent from the chamber into the intake air pathway through the delivery pathway.

2. The modified breathing apparatus of claim 1 wherein the breathing apparatus is a second stage regulator for scuba diving.

3. The modified breathing apparatus of claim 2 further comprising a balance means for substantially equalizing pressure in the chamber with ambient pressure.

4. The modified breathing apparatus of claim 1 wherein the breathing apparatus is a self-contained breathing apparatus (SCBA) suitable for use in firefighting and rescue, industry, shipping, mining, mountaineering, hazardous environment, aircraft and/or conditions of higher or lower atmospheric pressure.

5. The modified breathing apparatus of claim 1 wherein the medication chamber is sealed to resist entry of water, mud, dust or other contaminants.

6. The modified breathing apparatus of claim 5, wherein the therapeutic agent is housed in a container, said container adapted to be located in the medication chamber.

7. The modified breathing apparatus of claim 6 wherein the container comprises a capsule, a vial, a gelatine capsule or a blister pack.

8. The modified breathing apparatus of claim 6 wherein the container for housing the therapeutic agent is a pressurized canister.

9. The modified breathing apparatus of claim 8 wherein the pressurized canister has a release valve which is pressure activated to discharge the therapeutic agent.

10. The modified breathing apparatus of claim 8 wherein the releasing means comprises a rotatable control for activating a displacement mechanism to displace one of the pressurized canister and a seat co-operating with the canister and thereby activate the release valve of the pressurized canister.

11. The modified breathing apparatus of claim 10 wherein the displacement means is a cam operated slide positioned in the medication chamber.

12. The modified breathing apparatus of claim 8 wherein the releasing means includes a pressure activated button for displacing one of the canister and a seat cooperating with the canister to discharge the therapeutic agent through a release valve of the pressurized container.

13. The modified breathing apparatus of claim 1 wherein the medication chamber is formed integrally with the breathing apparatus.

14. The modified breathing apparatus of claim 1 wherein the medication chamber is formed for releasable engagement with the breathing apparatus.

15. The modified breathing apparatus of claim 1 wherein the therapeutic agent is one or more of albuterol, salbutamol, adrenaline, beconase or glucose.

16. The modified breathing apparatus of claim 1 wherein the delivery pathway is formed by the chamber being disposed along the intake airway or pathway.

17. The modified breathing apparatus of claim 1 wherein the delivery pathway is a bore, channel or aperture.

18. The modified breathing apparatus of claim 17 wherein the delivery pathway includes valve means operable to open and close the bore, channel or aperture.

19. The modified breathing apparatus of claim 18 wherein depression of the pressure activated button or rotation of the rotatable control rotates a delivery chute into a discharge position from an inactive position.

20. The modified breathing apparatus of claim 1 further including counting means for indicating the number of doses of therapeutic agent that have been discharged from the medication chamber.

21. The modified breathing apparatus of claim 20 wherein the counting means is formed as one or apertures in the chamber wall with moveable indicia visible therethrough, said moveable indicia providing an indication of either or both the number of dosages discharged from the chamber or the level of residual therapeutic agent in the chamber.

22. The modified breathing apparatus of claim 1 including a mouthpiece, said mouthpiece formed to provide separation between the teeth of a user, having an upper shield for receiving the upper teeth and a lower shield for receiving the lower teeth and an inlet aperture positioned between the upper and lower shields.

23. A medication chamber for use in medicating an air stream, the medication chamber comprising:
   a) an outer housing defining an internal chamber containing a therapeutic agent;
   b) mounting means for fixing the medication chamber to an air channelling device, said air channelling device comprising a regulator adapted for use in scuba gear, aircraft applications, gas masks, hazardous environments, mountaineering, power assisted respirators;
   c) at least one delivery path from the internal chamber externally and adapted to deliver the therapeutic agent to an air pathway in the air channelling device; and
   d) releasing means for releasing the therapeutic agent from the internal chamber.

24. The medication chamber of claim 23 including one or more of:
   a) the outer housing~formed of metal, plastic or polyvinyl chloride;
   b) the internal chamber sealed to resist entry of water, mud, dust or other contaminants;
   c) the outer housing formed as two inter-engageable sections;
   d) the therapeutic agent being any one of more of salbutamol, beconase, adrenaline, aminophylline or glucose;
   e) the outer housing including an inlet pathway for receiving a pressurized air supply into the internal chamber; and
   f) the outer housing including an outlet valve for discharging air from the internal chamber when air pressure inside the chamber exceeds the pressure outside the internal chamber.

25. The medication chamber of claim 23 wherein the therapeutic agent is held in a pressurized container having a release valve, the pressurized container locatable inside the outer housing.

26. The medication chamber of claim 25 wherein the releasing means includes a rotatable dial for activating a cammed mechanism to displace the canister and operate the release valve to thereby discharge a dose of therapeutic agent.

27. The medication chamber of claim 25 wherein the releasing means includes a pressure activated button for displacing the canister or the seat and activating the release valve.

28. A method of medicating an air stream in a breathing apparatus comprising a regulator suitable for delivering air from a source of compressed air, the regulator adapted for use in at least one of scuba gear, aircraft applications, gas masks, hazardous environments, mountaineering, power assisted respirators and a self-contained breathing apparatus, the method comprising the steps of mounting a chamber containing a therapeutic agent to a breathing apparatus and introducing one or more doses of the therapeutic agent into an inlet pathway for inspiratory air.

29. The method of claim 28 wherein the step of introducing one or more doses of the therapeutic agent into an inlet pathway comprises the step of introducing the therapeutic agent directly into the inlet pathway from the chamber or through a delivery air pathway from the chamber to the inlet pathway.

* * * * *